US010206800B2

(12) United States Patent
Wubbeling et al.

(10) Patent No.: US 10,206,800 B2
(45) Date of Patent: *Feb. 19, 2019

(54) DEVICE FOR CATHETER SHEATH RETRACTION

(71) Applicant: C. R. Bard, Inc., Tempe, AZ (US)

(72) Inventors: Martin Wubbeling, Mannheim (DE); Michael Vogel, Karlsruhe (DE); Jurgen Dorn, Neulussheim (DE)

(73) Assignee: C.R. Bard, Inc., Murray Hill, NJ (US)

( * ) Notice: Subject to any disclaimer, the term of this patent is extended or adjusted under 35 U.S.C. 154(b) by 316 days.

This patent is subject to a terminal disclaimer.

(21) Appl. No.: 14/793,659

(22) Filed: Jul. 7, 2015

(65) Prior Publication Data

US 2015/0320579 A1 Nov. 12, 2015

Related U.S. Application Data

(63) Continuation of application No. 13/958,460, filed on Aug. 3, 2013, now Pat. No. 9,421,115, which is a
(Continued)

(30) Foreign Application Priority Data

Jul. 11, 2007 (GB) .................................... 0713497.6

(51) Int. Cl.
   *A61F 2/95*      (2013.01)
   *A61F 2/966*     (2013.01)
   *A61M 25/01*     (2006.01)

(52) U.S. Cl.
   CPC ................ *A61F 2/95* (2013.01); *A61F 2/966* (2013.01); *A61M 25/0136* (2013.01); *A61F 2002/9517* (2013.01)

(58) Field of Classification Search
   CPC .... A61F 2/95; A61F 2/966; A61F 2002/9517; A61M 25/0113
   See application file for complete search history.

(56) References Cited

U.S. PATENT DOCUMENTS

| 1,988,060 A | 1/1935 | Vollenbroich |
| 2,934,211 A | 4/1960 | Shivek |
(Continued)

FOREIGN PATENT DOCUMENTS

| CA | 2155527 A1 | 8/1994 |
| DE | 1775056 A1 | 3/1972 |
(Continued)

OTHER PUBLICATIONS

U.S. Appl. No. 11/652,737, filed Jan. 12, 2007 Non-Final Office Action dated Nov. 12, 2018.
(Continued)

*Primary Examiner* — Katherine Rodjom
(74) *Attorney, Agent, or Firm* — Rutan & Tucker, LLP

(57) ABSTRACT

A device for moving an elongate member relative to an elongate body through which it extends, the device including a housing, a mover, and a pre-mover. The housing is connectable to the elongate body. The mover is associated with the housing and is connectable to the elongate member for moving the elongate member relative to the housing. The pre-mover is associated with the housing and is connectable to the elongate member for adjusting the elongate member in preparation for moving the elongate member with the mover.

8 Claims, 10 Drawing Sheets

Related U.S. Application Data continuation of application No. 12/668,613, filed as application No. PCT/EP2008/059040 on Jul. 10, 2008, now Pat. No. 8,500,789.

(56) References Cited

U.S. PATENT DOCUMENTS

| | | |
|---|---|---|
| 2,939,680 A | 6/1960 | Powell |
| 3,070,057 A | 12/1962 | Dezzani |
| 3,562,427 A | 2/1971 | Yano et al. |
| 3,585,707 A | 6/1971 | Stevens |
| 3,871,382 A | 3/1975 | Mann |
| 3,881,423 A | 5/1975 | Woods et al. |
| 4,256,113 A | 3/1981 | Chamness |
| 4,553,545 A | 11/1985 | Maass et al. |
| 4,580,568 A | 4/1986 | Gianturco |
| 4,616,648 A | 10/1986 | Simpson |
| 4,649,922 A | 3/1987 | Wiktor |
| 4,665,918 A | 5/1987 | Garza et al. |
| 4,723,547 A | 2/1988 | Kullas et al. |
| 4,733,665 A | 3/1988 | Palmaz |
| 4,739,762 A | 4/1988 | Palmaz |
| 4,748,982 A | 6/1988 | Horzewski et al. |
| 4,760,622 A | 8/1988 | Rohrman |
| 4,771,773 A | 9/1988 | Kropf |
| 4,800,882 A | 1/1989 | Gianturco |
| 4,856,516 A | 8/1989 | Hillstead |
| 4,886,062 A | 12/1989 | Wiktor |
| 4,889,112 A | 12/1989 | Schachner et al. |
| 4,913,141 A | 4/1990 | Hillstead |
| 4,913,683 A | 4/1990 | Gregory |
| 4,921,483 A | 5/1990 | Wijay et al. |
| 4,969,458 A | 11/1990 | Wiktor |
| 4,990,151 A | 2/1991 | Wallsten |
| 5,019,090 A | 5/1991 | Pinchuk |
| 5,026,377 A | 6/1991 | Burton et al. |
| 5,045,072 A | 9/1991 | Castillo et al. |
| 5,049,128 A | 9/1991 | Duquette |
| 5,054,162 A | 10/1991 | Rogers |
| 5,102,417 A | 4/1992 | Palmaz |
| 5,104,404 A | 4/1992 | Wolff |
| 5,116,365 A | 5/1992 | Hillstead |
| 5,133,732 A | 7/1992 | Wiktor |
| 5,135,536 A | 8/1992 | Hillstead |
| 5,161,547 A | 11/1992 | Tower |
| 5,163,941 A | 11/1992 | Garth et al. |
| 5,190,552 A | 3/1993 | Kelman |
| 5,201,757 A | 4/1993 | Heyn et al. |
| 5,203,774 A | 4/1993 | Gilson et al. |
| 5,209,754 A | 5/1993 | Ahluwalia |
| 5,224,939 A | 7/1993 | Holman et al. |
| 5,228,452 A | 7/1993 | Samson |
| 5,242,423 A | 9/1993 | Goodsir et al. |
| 5,254,107 A | 10/1993 | Soltesz |
| 5,275,622 A | 1/1994 | Lazarus et al. |
| 5,279,596 A | 1/1994 | Castaneda et al. |
| 5,282,824 A | 2/1994 | Gianturco |
| 5,290,295 A | 3/1994 | Querals et al. |
| 5,290,310 A | 3/1994 | Makower et al. |
| 5,292,331 A | 3/1994 | Boneau |
| 5,312,351 A | 5/1994 | Gerrone |
| 5,312,363 A | 5/1994 | Ryan et al. |
| 5,334,147 A | 8/1994 | Johnson |
| 5,336,192 A | 8/1994 | Palestrant |
| 5,346,498 A | 9/1994 | Greelis et al. |
| 5,370,655 A | 12/1994 | Burns |
| 5,380,283 A | 1/1995 | Johnson |
| 5,383,892 A | 1/1995 | Cardon et al. |
| 5,387,235 A | 2/1995 | Chuter |
| 5,391,172 A | 2/1995 | Williams et al. |
| 5,399,164 A | 3/1995 | Snoke et al. |
| 5,405,378 A | 4/1995 | Strecker et al. |
| 5,411,507 A | 5/1995 | Heckele |
| 5,415,664 A | 5/1995 | Pinchuk |
| 5,417,708 A | 5/1995 | Hall et al. |
| 5,421,955 A | 6/1995 | Lau et al. |
| 5,433,723 A | 7/1995 | Lindenberg et al. |
| 5,443,477 A | 8/1995 | Mann et al. |
| 5,445,646 A | 8/1995 | Euteneuer et al. |
| 5,449,366 A | 9/1995 | Li |
| 5,449,373 A | 9/1995 | Pinchasik et al. |
| 5,456,694 A | 10/1995 | Marin et al. |
| 5,456,713 A | 10/1995 | Chuter |
| 5,458,615 A | 10/1995 | Klemm et al. |
| 5,466,221 A | 11/1995 | Zadini et al. |
| 5,470,315 A | 11/1995 | Adams |
| 5,477,856 A | 12/1995 | Lundquist |
| 5,480,423 A | 1/1996 | Ravenscroft et al. |
| 5,484,444 A | 1/1996 | Braunschweiler et al. |
| 5,507,751 A | 4/1996 | Goode et al. |
| 5,507,768 A | 4/1996 | Lau et al. |
| 5,507,769 A | 4/1996 | Mahn et al. |
| 5,509,900 A | 4/1996 | Kirkman |
| 5,514,154 A | 5/1996 | Lau et al. |
| 5,531,690 A | 7/1996 | Solar |
| 5,534,007 A | 7/1996 | St. Germain et al. |
| 5,536,248 A | 7/1996 | Weaver et al. |
| 5,538,510 A | 7/1996 | Fontirroche et al. |
| 5,542,924 A | 8/1996 | Snoke et al. |
| 5,556,389 A | 9/1996 | Liprie |
| 5,562,726 A | 10/1996 | Chuter |
| 5,562,728 A | 10/1996 | Lazarus et al. |
| 5,569,296 A | 10/1996 | Marin et al. |
| 5,571,086 A | 11/1996 | Kaplan et al. |
| 5,571,172 A | 11/1996 | Chin |
| 5,573,530 A | 11/1996 | Fleury et al. |
| 5,578,074 A | 11/1996 | Mirigian |
| 5,591,172 A | 1/1997 | Bachmann et al. |
| 5,591,196 A | 1/1997 | Mahn et al. |
| 5,601,568 A | 2/1997 | Chevillon et al. |
| 5,603,721 A | 2/1997 | Lau et al. |
| 5,603,801 A | 2/1997 | DeFriese et al. |
| 5,605,530 A | 2/1997 | Fischell et al. |
| 5,609,627 A | 3/1997 | Goicoechea et al. |
| 5,618,300 A | 4/1997 | Marin et al. |
| 5,628,755 A | 5/1997 | Heller et al. |
| 5,630,801 A | 5/1997 | Roussigne et al. |
| 5,645,076 A | 7/1997 | Yoon |
| 5,649,906 A | 7/1997 | Gory et al. |
| 5,666,970 A | 9/1997 | Smith |
| 5,669,936 A | 9/1997 | Lazarus |
| 5,672,179 A | 9/1997 | Garth et al. |
| 5,674,208 A | 10/1997 | Berg et al. |
| 5,674,278 A | 10/1997 | Boneau |
| 5,681,322 A | 10/1997 | Hartigan, Jr. |
| 5,683,345 A | 11/1997 | Waksman et al. |
| 5,683,451 A | 11/1997 | Lenker et al. |
| 5,690,644 A | 11/1997 | Yurek et al. |
| 5,693,084 A | 12/1997 | Chuter |
| 5,695,498 A | 12/1997 | Tower |
| 5,695,499 A | 12/1997 | Helgerson et al. |
| 5,695,517 A | 12/1997 | Marin et al. |
| 5,697,936 A | 12/1997 | Shipko et al. |
| 5,697,949 A | 12/1997 | Giurtino et al. |
| 5,704,914 A | 1/1998 | Stocking et al. |
| 5,707,376 A | 1/1998 | Kavteladze et al. |
| 5,709,703 A | 1/1998 | Lukic et al. |
| 5,713,917 A | 2/1998 | Leonhardt et al. |
| 5,713,948 A | 2/1998 | Uflacker |
| 5,716,365 A | 2/1998 | Goicoechea et al. |
| 5,716,393 A | 2/1998 | Lindenberg et al. |
| 5,720,776 A | 2/1998 | Chuter et al. |
| 5,725,534 A | 3/1998 | Rasmussen |
| 5,728,158 A | 3/1998 | Lau et al. |
| 5,733,267 A | 3/1998 | Del Toro |
| 5,733,303 A | 3/1998 | Israel et al. |
| 5,735,893 A | 4/1998 | Lau et al. |
| 5,738,667 A | 4/1998 | Solar |
| 5,741,298 A | 4/1998 | MacLeod |
| 5,743,876 A | 4/1998 | Swanson |
| 5,749,921 A | 5/1998 | Lenker et al. |
| 5,755,777 A | 5/1998 | Chuter |
| 5,759,186 A | 6/1998 | Bachmann et al. |
| 5,766,184 A | 6/1998 | Matsuno et al. |
| 5,769,871 A | 6/1998 | Mers Kelly et al. |

(56) References Cited

U.S. PATENT DOCUMENTS

| | | |
|---|---|---|
| 5,776,141 A | 7/1998 | Klein et al. |
| 5,776,142 A | 7/1998 | Gunderson |
| 5,776,161 A | 7/1998 | Globerman et al. |
| 5,776,186 A | 7/1998 | Uflacker |
| 5,780,807 A | 7/1998 | Saunders |
| 5,782,855 A | 7/1998 | Lau et al. |
| 5,788,707 A | 8/1998 | Del Toro et al. |
| 5,795,325 A | 8/1998 | Valley et al. |
| 5,800,456 A | 9/1998 | Maeda et al. |
| 5,800,520 A | 9/1998 | Fogarty et al. |
| 5,807,241 A | 9/1998 | Heimberger et al. |
| 5,807,327 A | 9/1998 | Green et al. |
| 5,810,768 A | 9/1998 | Lopez |
| 5,810,837 A | 9/1998 | Hofmann et al. |
| 5,810,869 A | 9/1998 | Kaplan et al. |
| 5,810,872 A | 9/1998 | Kanesaka et al. |
| 5,814,062 A | 9/1998 | Sepetka et al. |
| 5,824,058 A | 10/1998 | Ravenscroft et al. |
| 5,833,694 A | 11/1998 | Poncet |
| 5,840,064 A | 11/1998 | Liprie |
| 5,843,088 A | 12/1998 | Barra et al. |
| 5,843,092 A | 12/1998 | Heller et al. |
| 5,843,120 A | 12/1998 | Israel et al. |
| 5,843,244 A | 12/1998 | Pelton et al. |
| 5,851,210 A | 12/1998 | Torossian |
| 5,860,998 A | 1/1999 | Robinson et al. |
| RE36,104 E | 2/1999 | Solar |
| 5,868,755 A | 2/1999 | Kanner et al. |
| 5,873,906 A | 2/1999 | Lau et al. |
| 5,879,382 A | 3/1999 | Boneau |
| 5,891,154 A | 4/1999 | Loeffler |
| 5,904,648 A | 5/1999 | Arndt et al. |
| 5,906,579 A | 5/1999 | Vander Salm et al. |
| 5,906,619 A | 5/1999 | Olson et al. |
| 5,910,145 A | 6/1999 | Fischell et al. |
| 5,913,897 A | 6/1999 | Corso, Jr. et al. |
| 5,919,225 A | 7/1999 | Lau et al. |
| 5,925,061 A | 7/1999 | Ogi et al. |
| 5,928,246 A | 7/1999 | Gordon et al. |
| 5,931,842 A | 8/1999 | Goldsteen et al. |
| 5,944,727 A | 8/1999 | Ahari et al. |
| 5,951,585 A | 9/1999 | Cathcart et al. |
| 5,954,729 A | 9/1999 | Bachmann et al. |
| 5,961,536 A | 10/1999 | Mickley et al. |
| 5,968,052 A | 10/1999 | Sullivan, III et al. |
| 5,968,053 A | 10/1999 | Revelas |
| 5,968,061 A | 10/1999 | Mirza |
| 5,968,068 A | 10/1999 | Dehdashtian et al. |
| 5,968,069 A | 10/1999 | Dusbabek et al. |
| 5,972,018 A | 10/1999 | Israel et al. |
| 5,980,515 A | 11/1999 | Tu |
| 5,984,225 A | 11/1999 | Enzinna |
| 5,992,000 A | 11/1999 | Humphrey et al. |
| 5,997,562 A | 12/1999 | Zadno-Azizi et al. |
| 6,004,328 A | 12/1999 | Solar |
| 6,015,429 A | 1/2000 | Lau et al. |
| 6,019,778 A | 2/2000 | Wilson et al. |
| 6,027,509 A | 2/2000 | Schatz et al. |
| 6,039,744 A | 3/2000 | Forber |
| 6,039,749 A | 3/2000 | Marin et al. |
| 6,042,597 A | 3/2000 | Kveen et al. |
| 6,045,536 A | 4/2000 | Meier et al. |
| 6,071,263 A | 6/2000 | Kirkman |
| 6,071,286 A | 6/2000 | Mawad |
| 6,077,295 A | 6/2000 | Limon et al. |
| 6,080,140 A | 6/2000 | Swaminathan et al. |
| 6,083,194 A | 7/2000 | Lopez |
| 6,090,035 A | 7/2000 | Campbell et al. |
| 6,090,063 A | 7/2000 | Makower et al. |
| 6,090,128 A | 7/2000 | Douglas |
| 6,096,009 A | 8/2000 | Windheuser et al. |
| 6,096,045 A | 8/2000 | Del Toro et al. |
| 6,096,056 A | 8/2000 | Brown |
| 6,102,890 A | 8/2000 | Stivland et al. |
| 6,102,942 A | 8/2000 | Ahari |
| 6,110,191 A | 8/2000 | Dehdashtian et al. |
| 6,113,607 A | 9/2000 | Lau et al. |
| 6,117,140 A | 9/2000 | Munsinger |
| 6,117,165 A | 9/2000 | Becker |
| 6,117,167 A | 9/2000 | Goicoechea et al. |
| 6,123,723 A | 9/2000 | Konya et al. |
| 6,129,755 A | 10/2000 | Mathis et al. |
| 6,136,007 A | 10/2000 | Goldsteen et al. |
| 6,136,572 A | 10/2000 | Benatti et al. |
| 6,143,014 A | 11/2000 | Dehdashtian et al. |
| 6,143,021 A | 11/2000 | Staehle |
| 6,146,415 A | 11/2000 | Fitz |
| 6,149,680 A | 11/2000 | Shelso et al. |
| 6,156,053 A | 12/2000 | Gandhi et al. |
| 6,156,054 A | 12/2000 | Zadno-Azizi et al. |
| 6,156,063 A | 12/2000 | Douglas |
| 6,159,228 A | 12/2000 | Frid et al. |
| 6,159,239 A | 12/2000 | Greenhalgh |
| 6,167,315 A | 12/2000 | Coe et al. |
| 6,168,610 B1 | 1/2001 | Marin et al. |
| 6,168,617 B1 | 1/2001 | Blaeser et al. |
| 6,174,327 B1 | 1/2001 | Mertens et al. |
| 6,183,509 B1 | 2/2001 | Dibie |
| 6,190,360 B1 | 2/2001 | Iancea et al. |
| 6,190,393 B1 | 2/2001 | Bevier et al. |
| 6,190,406 B1 | 2/2001 | Duerig et al. |
| 6,203,550 B1 | 3/2001 | Olson |
| 6,203,558 B1 | 3/2001 | Dusbabek et al. |
| 6,210,422 B1 | 4/2001 | Douglas |
| 6,214,026 B1 | 4/2001 | Lepak et al. |
| 6,217,585 B1 | 4/2001 | Houser et al. |
| 6,224,608 B1 | 5/2001 | Ciccolella et al. |
| 6,238,402 B1 | 5/2001 | Sullivan, III et al. |
| 6,238,415 B1 | 5/2001 | Sepetka et al. |
| 6,238,837 B1 | 5/2001 | Fan |
| 6,241,692 B1 | 6/2001 | Tu et al. |
| 6,245,100 B1 | 6/2001 | Davila et al. |
| 6,248,122 B1 | 6/2001 | Klumb et al. |
| 6,251,132 B1 | 6/2001 | Ravenscroft et al. |
| 6,254,608 B1 | 7/2001 | Solar |
| 6,264,689 B1 | 7/2001 | Colgan et al. |
| 6,270,521 B1 | 8/2001 | Fischell et al. |
| 6,273,879 B1 | 8/2001 | Keith et al. |
| 6,273,895 B1 | 8/2001 | Pinchuk et al. |
| 6,287,322 B1 | 9/2001 | Zhu et al. |
| 6,312,407 B1 | 11/2001 | Zadno-Azizi et al. |
| 6,319,262 B1 | 11/2001 | Bates et al. |
| 6,332,403 B1 | 12/2001 | Weise et al. |
| 6,342,067 B1 | 1/2002 | Mathis et al. |
| 6,344,053 B1 | 2/2002 | Boneau |
| 6,346,118 B1 | 2/2002 | Baker et al. |
| 6,348,065 B1 | 2/2002 | Brown et al. |
| 6,358,274 B1 | 3/2002 | Thompson |
| 6,368,344 B1 | 4/2002 | Fitz |
| 6,375,676 B1 | 4/2002 | Cox |
| 6,383,211 B1 | 5/2002 | Staehle |
| 6,391,050 B1 | 5/2002 | Broome |
| 6,391,051 B2 | 5/2002 | Sullivan, III et al. |
| 6,395,020 B1 | 5/2002 | Ley et al. |
| 6,402,760 B1 | 6/2002 | Fedida |
| 6,413,269 B1 | 7/2002 | Bui et al. |
| 6,425,898 B1 | 7/2002 | Wilson et al. |
| 6,443,979 B1 | 9/2002 | Stalker et al. |
| 6,443,982 B1 | 9/2002 | Israel et al. |
| 6,461,381 B2 | 10/2002 | Israel et al. |
| 6,471,673 B1 | 10/2002 | Kastenhofer |
| 6,488,703 B1 | 12/2002 | Kveen et al. |
| 6,500,248 B1 | 12/2002 | Hayashi |
| 6,514,261 B1 | 2/2003 | Randall et al. |
| 6,517,569 B2 | 2/2003 | Mikus et al. |
| 6,520,938 B1 | 2/2003 | Funderburk et al. |
| 6,520,983 B1 | 2/2003 | Colgan et al. |
| 6,527,779 B1 | 3/2003 | Rourke |
| 6,527,789 B1 | 3/2003 | Lau et al. |
| 6,544,278 B1 | 4/2003 | Vrba et al. |
| 6,569,181 B1 | 5/2003 | Burns |
| 6,572,643 B1 | 6/2003 | Gharibadeh |
| 6,575,993 B1 | 6/2003 | Yock |
| 6,582,459 B1 | 6/2003 | Lau et al. |

(56) References Cited

U.S. PATENT DOCUMENTS

| | | |
|---|---|---|
| 6,582,460 B1 | 6/2003 | Cryer |
| 6,599,296 B1 | 7/2003 | Gillick et al. |
| 6,613,014 B1 | 9/2003 | Chi |
| 6,613,075 B1 | 9/2003 | Healy et al. |
| 6,629,981 B2 | 10/2003 | Bui et al. |
| 6,645,238 B2 | 11/2003 | Smith |
| 6,652,506 B2 | 11/2003 | Bowe et al. |
| 6,659,977 B2 | 12/2003 | Kastenhofer |
| 6,660,031 B2 | 12/2003 | Tran et al. |
| 6,660,827 B2 | 12/2003 | Loomis et al. |
| 6,663,666 B1 | 12/2003 | Duiachon et al. |
| 6,695,862 B2 | 2/2004 | Cox et al. |
| 6,716,190 B1 | 4/2004 | Glines et al. |
| 6,716,238 B2 | 4/2004 | Elliott |
| 6,749,627 B2 | 6/2004 | Thompson et al. |
| 6,755,854 B2 | 6/2004 | Gillick et al. |
| 6,773,446 B1 | 8/2004 | Dwyer et al. |
| 6,786,918 B1 | 9/2004 | Krivoruchko et al. |
| 6,821,292 B2 | 11/2004 | Pazienza et al. |
| 6,866,669 B2 | 3/2005 | Buzzard et al. |
| 6,884,259 B2 | 4/2005 | Tran et al. |
| 6,911,039 B2 | 6/2005 | Shiu et al. |
| 6,913,613 B2 | 7/2005 | Schwarz et al. |
| 6,939,352 B2 | 9/2005 | Buzzard et al. |
| 6,939,370 B2 | 9/2005 | Hartley et al. |
| 7,033,368 B2 | 4/2006 | Rourke |
| 7,052,511 B2 | 5/2006 | Weldon et al. |
| 7,122,050 B2 | 10/2006 | Randall et al. |
| 7,172,617 B2 | 2/2007 | Colgan et al. |
| 7,294,135 B2 | 11/2007 | Stephens et al. |
| 7,323,006 B2 | 1/2008 | Andreas et al. |
| 7,381,216 B2 | 6/2008 | Buzzard et al. |
| D576,725 S | 9/2008 | Shumer et al. |
| D578,216 S | 10/2008 | Dom et al. |
| D578,643 S | 10/2008 | Shumer et al. |
| D578,644 S | 10/2008 | Shumer et al. |
| D578,645 S | 10/2008 | Shumer et al. |
| 7,506,650 B2 | 3/2009 | Lowe et al. |
| 7,550,001 B2 | 6/2009 | Dorn et al. |
| 7,553,322 B2 | 6/2009 | Dorn et al. |
| 7,556,641 B2 | 7/2009 | Cully et al. |
| D598,543 S | 8/2009 | Vogel et al. |
| 7,582,054 B2 | 9/2009 | Okada |
| 7,935,141 B2 | 5/2011 | Randall et al. |
| 8,062,344 B2 | 11/2011 | Dorn et al. |
| 8,075,606 B2 | 12/2011 | Dorn |
| 8,382,813 B2 | 2/2013 | Shumer |
| 8,419,784 B2 | 4/2013 | Matsuoka et al. |
| 8,500,789 B2 * | 8/2013 | Wuebbeling .............. A61F 2/95 606/108 |
| 8,808,346 B2 | 8/2014 | Jimenez, Jr. et al. |
| 9,421,115 B2 * | 8/2016 | Wuebbeling .............. A61F 2/95 |
| 2001/0007082 A1 | 7/2001 | Dusbabek et al. |
| 2001/0044621 A1 | 11/2001 | Klumb et al. |
| 2001/0051822 A1 | 12/2001 | Stack et al. |
| 2002/0004663 A1 | 1/2002 | Gittings et al. |
| 2002/0035394 A1 | 3/2002 | Fierens et al. |
| 2002/0045929 A1 | 4/2002 | Diaz |
| 2002/0052642 A1 | 5/2002 | Cox et al. |
| 2002/0116044 A1 | 8/2002 | Cottone et al. |
| 2002/0128678 A1 | 9/2002 | Petersen |
| 2002/0151955 A1 | 10/2002 | Tran et al. |
| 2002/0183827 A1 | 12/2002 | Derus et al. |
| 2002/0188341 A1 | 12/2002 | Elliott |
| 2003/0028236 A1 | 2/2003 | Gillick et al. |
| 2003/0049295 A1 | 3/2003 | Guggenbichler et al. |
| 2003/0050686 A1 | 3/2003 | Raeder-Devens et al. |
| 2003/0074043 A1 | 4/2003 | Thompson |
| 2003/0074045 A1 | 4/2003 | Buzzard et al. |
| 2003/0105451 A1 | 6/2003 | Westlund et al. |
| 2003/0135162 A1 | 7/2003 | Deyette et al. |
| 2003/0163085 A1 | 8/2003 | Tanner et al. |
| 2003/0167060 A1 | 9/2003 | Buzzard et al. |
| 2003/0191516 A1 | 10/2003 | Weldon et al. |
| 2003/0208262 A1 | 11/2003 | Gaber |
| 2004/0006380 A1 | 1/2004 | Buck et al. |
| 2004/0098079 A1 | 5/2004 | Hartley et al. |
| 2004/0098083 A1 | 5/2004 | Tran et al. |
| 2004/0143160 A1 | 7/2004 | Couvillon |
| 2004/0148009 A1 | 7/2004 | Buzzard et al. |
| 2004/0153137 A1 | 8/2004 | Gaschino et al. |
| 2004/0181239 A1 | 9/2004 | Dorn et al. |
| 2004/0186547 A1 | 9/2004 | Dorn et al. |
| 2004/0193180 A1 | 9/2004 | Buzzard et al. |
| 2004/0193283 A1 | 9/2004 | Rioux et al. |
| 2004/0199240 A1 | 10/2004 | Dorn |
| 2005/0004515 A1 | 1/2005 | Hart et al. |
| 2005/0021123 A1 | 1/2005 | Dorn et al. |
| 2005/0027306 A1 | 2/2005 | Krivoruchko et al. |
| 2005/0027345 A1 | 2/2005 | Horan et al. |
| 2005/0033402 A1 | 2/2005 | Cully et al. |
| 2005/0043618 A1 | 2/2005 | Mansouri-Ruiz |
| 2005/0043713 A1 | 2/2005 | Zhou |
| 2005/0060016 A1 | 3/2005 | Wu et al. |
| 2005/0080476 A1 | 4/2005 | Gunderson et al. |
| 2005/0085851 A1 | 4/2005 | Fiehler et al. |
| 2005/0090887 A1 | 4/2005 | Pryor |
| 2005/0090890 A1 | 4/2005 | Wu et al. |
| 2005/0149159 A1 | 7/2005 | Andreas et al. |
| 2005/0159725 A1 | 7/2005 | Tockman et al. |
| 2005/0182475 A1 | 8/2005 | Jen et al. |
| 2005/0209670 A1 | 9/2005 | George et al. |
| 2005/0209672 A1 | 9/2005 | George et al. |
| 2005/0209674 A1 | 9/2005 | Kutscher et al. |
| 2005/0240254 A1 | 10/2005 | Austin |
| 2005/0256562 A1 | 11/2005 | Clerc et al. |
| 2005/0273151 A1 | 12/2005 | Fulkerson et al. |
| 2005/0288764 A1 | 12/2005 | Snow et al. |
| 2006/0058866 A1 | 3/2006 | Cully et al. |
| 2006/0074477 A1 | 4/2006 | Berthiaume et al. |
| 2006/0085057 A1 | 4/2006 | George et al. |
| 2006/0095116 A1 | 5/2006 | Bolduc et al. |
| 2006/0100686 A1 | 5/2006 | Bolduc et al. |
| 2006/0167467 A1 | 7/2006 | Rourke |
| 2006/0173525 A1 | 8/2006 | Behl et al. |
| 2006/0241737 A1 | 10/2006 | Tockman et al. |
| 2006/0259124 A1 | 11/2006 | Matsuoka et al. |
| 2006/0276873 A1 | 12/2006 | Sato |
| 2007/0016164 A1 | 1/2007 | Dudney et al. |
| 2007/0050006 A1 | 3/2007 | Lavelle |
| 2007/0055339 A1 | 3/2007 | George et al. |
| 2007/0055342 A1 | 3/2007 | Wu et al. |
| 2007/0060999 A1 | 3/2007 | Randall et al. |
| 2007/0073379 A1 | 3/2007 | Chang |
| 2007/0073389 A1 | 3/2007 | Bolduc et al. |
| 2007/0088421 A1 | 4/2007 | Loewen |
| 2007/0100420 A1 | 5/2007 | Kavanagh et al. |
| 2007/0100422 A1 | 5/2007 | Shumer et al. |
| 2007/0100429 A1 | 5/2007 | Wu et al. |
| 2007/0112409 A1 | 5/2007 | Wu et al. |
| 2007/0118201 A1 | 5/2007 | Pappas et al. |
| 2007/0118206 A1 | 5/2007 | Colgan et al. |
| 2007/0156222 A1 | 7/2007 | Feller et al. |
| 2007/0156224 A1 | 7/2007 | Cioanta et al. |
| 2007/0168014 A1 | 7/2007 | Jimenez et al. |
| 2007/0191864 A1 | 8/2007 | Shumer |
| 2007/0191865 A1 | 8/2007 | Pappas |
| 2007/0191925 A1 | 8/2007 | Dorn |
| 2007/0194483 A1 | 8/2007 | Guggenbichler et al. |
| 2007/0233222 A1 | 10/2007 | Roeder et al. |
| 2007/0244540 A1 | 10/2007 | Pryor |
| 2007/0255390 A1 | 11/2007 | Ducke et al. |
| 2008/0188920 A1 | 8/2008 | Moberg et al. |
| 2009/0024133 A1 | 1/2009 | Keady et al. |
| 2009/0099638 A1 | 4/2009 | Grewe |
| 2010/0004606 A1 | 1/2010 | Hansen et al. |
| 2010/0036472 A1 | 2/2010 | Papp |
| 2010/0094399 A1 | 4/2010 | Dorn et al. |
| 2010/0161024 A1 | 6/2010 | Kennedy, II et al. |
| 2010/0168756 A1 | 7/2010 | Dorn et al. |
| 2010/0174290 A1 | 7/2010 | Wuebbeling et al. |

(56) References Cited

U.S. PATENT DOCUMENTS

| | | | |
|---|---|---|---|
| 2013/0317592 | A1 | 11/2013 | Wubbeling et al. |
| 2014/0330362 | A1 | 11/2014 | Jimenez, Jr. et al. |

FOREIGN PATENT DOCUMENTS

| | | | |
|---|---|---|---|
| DE | 02544371 | A1 | 4/1976 |
| DE | 03132323 | A1 | 4/1983 |
| DE | 3219629 | A1 | 12/1983 |
| DE | 1133696 | A1 | 4/1993 |
| DE | 04420142 | A1 | 12/1995 |
| DE | 29516712 | U1 | 12/1995 |
| DE | 19539449 | A1 | 4/1997 |
| DE | 29717110 | U1 | 11/1997 |
| DE | 29816878 | U1 | 12/1998 |
| DE | 29522101 | | 12/1999 |
| DE | 19921530 | | 6/2000 |
| DE | 19901530 | A1 | 7/2000 |
| DE | 19936059 | A1 | 2/2001 |
| DE | 20000659 | U1 | 5/2001 |
| DE | 59521346 | T2 | 4/2002 |
| EP | 0436303 | A1 | 7/1991 |
| EP | 0505686 | A1 | 9/1992 |
| EP | 0518838 | A1 | 12/1992 |
| EP | 0564894 | A1 | 10/1993 |
| EP | 0611556 | A1 | 8/1994 |
| EP | 0630657 | A1 | 12/1994 |
| EP | 0633756 | B1 | 1/1995 |
| EP | 0688545 | A1 | 12/1995 |
| EP | 0699451 | A2 | 3/1996 |
| EP | 0712614 | A1 | 5/1996 |
| EP | 0744930 | A1 | 12/1996 |
| EP | 0747021 | A2 | 12/1996 |
| EP | 0752896 | B1 | 1/1997 |
| EP | 0790041 | A2 | 8/1997 |
| EP | 0792627 | A2 | 9/1997 |
| EP | 0873733 | A1 | 10/1998 |
| EP | 0876804 | A1 | 11/1998 |
| EP | 0947212 | A2 | 10/1999 |
| EP | 1025813 | A2 | 8/2000 |
| EP | 1078611 | A1 | 2/2001 |
| EP | 1095634 | A2 | 5/2001 |
| EP | 1117341 | A1 | 7/2001 |
| EP | 1132058 | A1 | 9/2001 |
| EP | 1155664 | A2 | 11/2001 |
| EP | 1181906 | A2 | 2/2002 |
| EP | 1199051 | A2 | 4/2002 |
| EP | 1290989 | A2 | 3/2003 |
| EP | 1299050 | B1 | 4/2003 |
| EP | 1302178 | A2 | 4/2003 |
| EP | 1383446 | A1 | 1/2004 |
| EP | 1440671 | A2 | 7/2004 |
| EP | 1447057 | A1 | 8/2004 |
| EP | 1447058 | A1 | 8/2004 |
| EP | 1637092 | A2 | 3/2006 |
| FR | 2760351 | A1 | 9/1998 |
| FR | 2797761 | A1 | 3/2001 |
| JP | 2003518406 | A | 6/2003 |
| JP | 2004147812 | A | 5/2004 |
| JP | 2005530558 | A | 10/2005 |
| JP | 2005532100 | A | 10/2005 |
| JP | 2007-097620 | A | 4/2007 |
| JP | 2007-508045 | A | 4/2007 |
| MX | 303207 | | 12/2012 |
| WO | 1995021593 | A1 | 8/1995 |
| WO | 1995026775 | A1 | 10/1995 |
| WO | 1996018359 | A1 | 6/1996 |
| WO | 1996018361 | A1 | 6/1996 |
| WO | 1998009584 | A1 | 3/1998 |
| WO | 1998020811 | A1 | 5/1998 |
| WO | 1998023241 | A2 | 6/1998 |
| WO | 1998030173 | A1 | 7/1998 |
| WO | 1998052496 | A1 | 11/1998 |
| WO | 1999004728 | A1 | 2/1999 |
| WO | 1999025280 | A1 | 5/1999 |
| WO | 1999044541 | A1 | 9/1999 |
| WO | 1999047075 | A1 | 9/1999 |
| WO | 1999051167 | A2 | 10/1999 |
| WO | 2000000104 | A1 | 1/2000 |
| WO | 2000002503 | A1 | 1/2000 |
| WO | 2000016718 | A1 | 3/2000 |
| WO | 2000018330 | A1 | 4/2000 |
| WO | 2000067675 | A1 | 11/2000 |
| WO | 2000069368 | A2 | 11/2000 |
| WO | 2000071059 | A1 | 11/2000 |
| WO | 2000078246 | A2 | 12/2000 |
| WO | 2000078248 | A1 | 12/2000 |
| WO | 2001032102 | A1 | 5/2001 |
| WO | 2001034061 | A1 | 5/2001 |
| WO | 2001047436 | A2 | 7/2001 |
| WO | 2001058387 | A1 | 8/2001 |
| WO | 2001089421 | | 11/2001 |
| WO | 2002003888 | A2 | 1/2002 |
| WO | 2002003889 | A2 | 1/2002 |
| WO | 2002066094 | A2 | 8/2002 |
| WO | 2002083036 | A2 | 10/2002 |
| WO | 2002087470 | A1 | 11/2002 |
| WO | 2002102279 | A2 | 12/2002 |
| WO | 2003002020 | A2 | 1/2003 |
| WO | 2003003926 | A1 | 1/2003 |
| WO | 2003061724 | A2 | 7/2003 |
| WO | 2004004597 | A2 | 1/2004 |
| WO | 2004066809 | A2 | 8/2004 |
| WO | 2005039448 | A1 | 5/2005 |
| WO | 2005053574 | A2 | 6/2005 |
| WO | 2005062980 | A2 | 7/2005 |
| WO | 2005065200 | A2 | 7/2005 |
| WO | 2005117759 | A2 | 12/2005 |
| WO | 2006071915 | A2 | 7/2006 |
| WO | 2006104143 | A1 | 10/2006 |
| WO | 2007002713 | A2 | 1/2007 |
| WO | 2007005799 | A1 | 1/2007 |
| WO | 2007022395 | A1 | 2/2007 |
| WO | 2007029242 | A1 | 3/2007 |
| WO | 2007044929 | A1 | 4/2007 |
| WO | 2007083470 | A1 | 7/2007 |
| WO | 2008034793 | A1 | 3/2008 |
| WO | 2010027998 | A1 | 3/2010 |

OTHER PUBLICATIONS

U.S. Appl. No. 11/652,737, filed Jan. 12, 2007 Non-Final Office Action dated Apr. 12, 2013.
U.S. Appl. No. 11/652,737, filed Jan. 12, 2007 Non-Final Office Action dated Feb. 12, 2014.
U.S. Appl. No. 11/652,737, filed Jan. 12, 2007 Advisory Action dated Dec. 30, 2013.
U.S. Appl. No. 11/652,737, filed Jan. 12, 2007 Final Office Action dated Oct. 22, 2013.
U.S. Appl. No. 11/652,737, filed Jan. 12, 2007 Notice of Allowance dated Apr. 25, 2014.
U.S. Appl. No. 12/376,670, filed Feb. 6, 2009 Final Office Action dated Dec. 17, 2013.
U.S. Appl. No. 12/376,670, filed Feb. 6, 2009 Non-Final Office Action dated Jun. 21, 2012.
U.S. Appl. No. 12/640,956, filed Dec. 17, 2009 Non-Final Office Action dated Jan. 24, 2011.
U.S. Appl. No. 12/640,956, filed Dec. 17, 2009 Notice of Allowancwe dated Jul. 13, 2011.
U.S. Appl. No. 12/668,613, filed Feb. 19, 2010 Non-Final Office Action dated Nov. 26, 2012.
U.S. Appl. No. 13/958,460, filed Aug. 2, 2013 Non-Final Office Action dated Dec. 4, 2015.
U.S. Appl. No. 13/958,460, filed Aug. 2, 2013 Notice of Allowance dated Apr. 22, 2016.
"Medtronic Announces FDA Clearance of Bridge SE Biliary Stent." Business Wire, Oct 15, 2001. www.medtronc.com/newsroom/news_20011015a.html.
"Summary for the Bridge SE Biliary Self-Expanding Stent Delivery System" Jan. 14, 2002 FDA Section 510 (k) review.
Bridge™ SE Binary Stent System, «http:/www.medtronicave/com/includes/content/phsycians/bridges/htm», 3 pages, last accessed Oct. 2002.

(56) References Cited

OTHER PUBLICATIONS

Ep 10001359.8 filed Aug. 8, 2006 European Search Report dated May 28, 2010.
EP 13170019.7 extended European Search Report dated Aug. 5, 2013.
EP 14151266.5 extended European Search Report dated Apr. 9, 2014.
JP 2008-550429 filed Jun. 27, 2008 Final Notice of Reason for Rejection dated Oct. 25, 2012.
JP 2008-550429 filed Jun. 27, 2008 Office Action dated Jan. 4, 2012.
JP 2010-515514 Notice of Reason for Rejection dated Dec. 20, 2012.
JP 2013-011060 first Official Action dated Feb. 21, 2014.
JP 2013-089100 Official Action dated Apr. 8, 2014.
PCT/EP2002/004727 filed Apr. 29, 2002 Preliminary Examination Report dated Jan. 7, 2003.
PCT/EP2002/004727 filed Apr. 29, 2002 Search Report dated Jul. 10, 2002.
PCT/EP2002/006784 filed Jun. 19, 2002 Preliminary Examination Report dated Apr. 14, 2004.
PCT/EP2002/006784 filed Jun. 19, 2002 Search Report dated Jan. 21, 2004.
PCT/EP2007/058205 filed Aug. 7, 2007 Preliminary Report on Patentability dated Aug. 4, 2008.
PCT/EP2007/058205 filed Aug. 7, 2007 Search Report dated Nov. 30, 2007.
PCT/EP2007/058205 filed Aug. 7, 2007 Written Opinion Nov. 30, 2007.
PCT/EP2008/059040 filed Jul. 1, 2008 Search Report dated Nov. 4, 2008.
PCT/EP2008/059040 filed Jul. 10, 2008 Preliminary Report on Patentability dated Sep. 29, 2009.
PCT/EP2008/059040 filed Jul. 10, 2008 Written Opinion dated Nov. 4, 2008.
PCT/EP2011/068238 filed Oct. 19, 2011 International Preliminary Report on Patentability dated Apr. 23, 2013.
PCT/US2005/019860 filed Jun. 6, 2005 Preliminary Report on Patentability dated Dec, 4, 2006.
PCT/US2005/019860 filed Jun. 6, 2005 Search Report dated Dec. 15, 2005.
PCT/US2005/019860 filed Jun. 6, 2006 Written Opinion dated Dec. 15, 2005.
PCT/US2006/032228 filed Aug. 16, 2006 Preliminary Report on Patentability dated Feb. 20, 2008.
PCT/US2006/032228 filed Aug. 16, 2006 Search Report dated Jan. 19, 2007.
PCT/US2006/032228 filed Aug. 16, 2006 Written Opinion dated Jan. 19, 2007.
PCT/US2007/000834 filed Jan. 12, 2007 Preliminary Report on Patentability Jul. 15, 2008.
PCT/US2007/000834 filed Jan. 12, 2007 Search Report dated Apr. 27, 2007.
PCT/US2007/000834 filed Jan. 12, 2007 Written Opinion dated Apr. 27, 2007.
U.S. Appl. No. 10/476,351, filed May 7, 2004 Final Office Action dated Feb. 4, 2009.
U.S. Appl. No. 10/476,351, filed May 7, 2004 Final Office Action dated Oct. 21, 2008.
U.S. Appl. No. 10/476,351, filed May 7, 2004 Non-Final Office Action dated Apr. 4, 2008.
U.S. Appl. No. 10/476,351, filed May 7, 2004 Notice of Allowance dated Mar. 12, 2009.
U.S. Appl. No. 10/824,033, filed Apr. 14, 2004 Non-Final Office Action dated Jul. 17, 2009.
U.S. Appl. No. 11/144,513, filed Jun. 3, 2005 Advisory Action dated Oct. 5, 2010.
U.S. Appl. No. 11/144,513, filed Jun. 3, 2005 Final Office Action dated Jul. 13, 2010.
U.S. Appl. No. 11/144,513, filed Jun. 3, 2005 Final Office Action dated Oct. 15, 2008.
U.S. Appl. No. 11/144,513, filed Jun. 3, 2005 Final Office Action dated Oct. 20, 2009.
U.S. Appl. No. 11/144,513, filed Jun. 3, 2005 Non-Final Office Action dated Feb. 2, 2010.
U.S. Appl. No. 11/144,513, filed Jun. 3, 2005 Non-Final Office Action dated Feb. 5, 2008.
U.S. Appl. No. 11/144,513, filed Jun. 3, 2005 Non-Final Office Action dated Feb. 26, 2009.
U.S. Appl. No. 11/505,185, filed Aug. 16, 2006 Non-Final Office Action dated Mar. 31, 2010.
U.S. Appl. No. 11/505,185, filed Aug. 16, 2006 Non-Final Office Action dated Aug. 31, 2009.
U.S. Appl. No. 11/505,185, filed Aug. 16, 2006 Non-Final Office Action dated Oct. 7, 2010.
U.S. Appl. No. 11/652,737, filed Jan. 12, 2007 Advisory Action dated Aug. 27, 2010.
U.S. Appl. No. 11/652,737, filed Jan. 12, 2007 Final Office Action dated May 27, 2009.
U.S. Appl. No. 11/652,737, filed Jan. 12, 2007 Final Office Action dated Jun. 10, 2010.
U.S. Appl. No. 11/652,737, filed Jan. 12, 2007 Non-Final Office Action dated Oct. 27, 2009.
EP 14151266.5 filed Jan. 14, 2014, Examination Report dated Oct. 2, 2018.
U.S. Appl. No. 15/473,420, filed Mar. 29, 2017 Non-Final Office Action dated Sep. 26, 2018.

* cited by examiner

DEVICE FOR CATHETER SHEATH RETRACTION

PRIORITY

This application is a continuation of U.S. patent application Ser. No. 13/958,460, filed Aug. 2, 2013, now U.S. Pat. No. 9,421,115, which is a continuation of U.S. patent application Ser. No. 12/668,613, filed Feb. 19, 2010, now U.S. Pat. No. 8,500,789, filed as a U.S. national stage application under 35 USC § 371 of International Application No. PCT/EP2008/059040, filed Jul. 10, 2008, claiming priority to Great Britain Patent Application No. 0713497.6, filed Jul. 11, 2007, each of which is incorporated by reference in its entirety into this application.

FIELD OF THE INVENTION

The present invention relates to a device for moving an elongate member relative to an elongate body through which it at least partially extends, to a device for moving an elongate member by a predetermined distance relative to an elongate body through which it at least partially extends, thereby to release a stent at the distal end of the elongate body, and to surgical apparatus including such devices. More specifically, the invention is concerned with medical transluminal catheters such as those used to deliver a stent to a vascular treatment location, and the devices by which a medical practitioner operates such catheters from a location external of the patient.

BACKGROUND OF THE INVENTION

It has long been desirable to reduce the degree of trauma caused by, and attendant risks associated with, surgical procedures. In order to further this aim, there have been a large number of technical advances in recent times to enable various surgical procedures to be carried out using minimally invasive techniques.

One particular form of treatment to have benefited from advances in minimally invasive surgical procedures is the treatment of cardiovascular diseases. Whereas in the past it would have been necessary to conduct an open procedure in order to access the heart or a portion of the venous system, minimally invasive techniques have now been developed in which a catheter-based piece of surgical equipment can be deployed to a treatment location within a patient's cardiovascular system from a remote location external to the patient. Specifically, an elongate endoluminal catheter is inserted percutaneously through an incision in a patient's skin and is then advanced transluminally through the patient's vasculature from the incision location to a treatment location. A control device, mounted at the proximal end of the surgical catheter, is used to control the equipment mounted at the distal end of the surgical catheter, which has been advanced to the treatment location, from a remote location external to the patient's body.

In one particular technique, a stent is mounted on a distal end portion of the surgical catheter in a reduced-diameter configuration. The surgical catheter includes a retractable sheath which extends along at least the distal portion of the catheter to enclose the stent and to retain the stent in the reduced-diameter configuration. When the catheter distal portion has been advanced to the treatment location, the sheath is retracted to expose the stent. The stent is then caused to expand to an increased-diameter configuration at the treatment location, so that its abluminal surface engages the vessel inner wall, and thereafter serves to maintain an open fluid passageway through the vascular treatment location. The surgical catheter is then retrieved from the patient, leaving the stent in place. Preferably the stent is a so-called self-expanding stent, typically manufactured from a shape memory alloy, such as Nitinol, and being configured to expand from the reduced diameter configuration to the increased-diameter configuration due to the memorized molecular configuration of the alloy at body temperature. When the sheath is retracted, such a stent therefore adopts the increased-diameter configuration without further intervention by the medical practitioner. Balloon-expandable stents, and other configurations, are also known, however, which require intervention by the medical practitioner to cause the stent to expand from the reduced-diameter configuration to the increased-diameter configuration.

In order to be insertable through the tortuous vasculature of a patient, from the mc1s10n location to the treatment site, a surgical catheter must be flexible transverse to its longitudinal axis. This allows the catheter to follow the narrow and twisting passageways through the patient's venous system. On the other hand, such catheters must be relatively incompressible in the lengthwise direction, so as to facilitate catheter advancement by providing a driving force to guide the catheter into the vasculature from the proximal end, and so as to resist compression during retraction of the catheter sheath when a stent is to be released. For this purpose, it is not uncommon to provide a means of reinforcing the inner tubular portion of the surgical catheter, such as by providing a coil spring along the length thereof from the proximal end to the distal portion. Such a coil spring is closely wound, with adjacent turns of the coil being substantially in contact with one another, to resist compressive forces but provides the requisite degree of flexibility transverse to the coil's central axis. A so-called stent pusher may be provided at the coil distal end, configured to engage the stent and to prevent proximal displacement of the stent when a retaining sheath is withdrawn for stent release.

The sheath provided to restrain the stent in the reduced diameter configuration may be provided so as to extend along the entire length of the surgical catheter, from the proximal end to the distal tip. On the other hand, the sheath need only be provided in a region at the distal portion of the catheter, sufficient to enclose the stent along its length, and being retractable to fully expose the stent. In either case, a sheath retraction wire may be provided by which to withdraw the sheath proximally along the catheter, thereby exposing the stent at the catheter distal end portion. Typically, as noted, the stent will be self-expanding, so as to place the sheath under a circumferential pre-tension. In order to allow the sheath to slide over the catheter, the catheter and sheath are usually constructed from low-friction materials, and provided with a lubricant or lubricious surface treatment there-between.

At the proximal end of the surgical catheter, a device is provided for retracting the sheath over the catheter. Typically, such a device includes a housing by which a medical practitioner can grip the device, and to which the catheter is rigidly connected. In particular, any reinforcing member, such as a coil spring, is attached to the device distal end by a hub, by which to hold the reinforcing member in place. A retraction wire is typically provided, attached at its distal end to one end of the catheter sheath, by which to withdraw the sheath. Typically, the retraction wire extends from the connection point with the sheath, into and through a lumen inside the catheter, to extend from the proximal end of the catheter inside the device housing. An actuator is provided, operable by the medical practitioner using the device, by which the sheath wire is retracted to withdraw the sheath and expose the distal portion of the catheter. In alternative configurations, a retraction wire is not necessitated, and the sheath may be connected directly to a portion of the actuator mechanism within the housing. In most applications, the catheter sheath is configured to be withdrawn proximally along the catheter, but distal withdrawal is not impossible. The reinforcing member serves to resist compression due to the tensile stresses in the catheter sheath and retraction wire. The resulting compressive stresses are transferred from the reinforcing member to the device via the connection hub by which they are joined.

WO 02/087470 A1 discloses a sheath refraction device for proximally withdrawing a catheter sheath. The sheath is in the form of an outer tube 16 connected at its proximal end to a slider 24 in the device housing. As the slider 24 is proximally withdrawn, the sheath is retracted. The retraction device in WO 02/087470 A1 provides two actuation mechanisms by which the sheath may be withdrawn. The first is to provide a finger engagement portion (a button) on the slider 24, by which the slider and the connected outer tube 16 may be directly proximally withdrawn by refracting the slider along slider tracks provided. The second mechanism by which the sheath may be withdrawn is actuated by a finger trigger 34. A pull wire 30 extends proximally from the slider 24 to a take-up reel 32. The take-up reel is connected to a toothed gear 35, which engages with ratchet teeth 36 of the trigger 34. When the trigger is depressed, the ratchet teeth rotate the toothed gear 35 so as to wind the pull wire 30 on the take-up reel 32, thereby retracting the slider and connected sheath proximally in the housing. Because the teeth 36 are ratchet teeth, the take-up reel may only be rotated in one direction by successive pulls of the trigger. The length of a retraction stroke possible with the device of WO 02/087470 A1 is restricted by the length of the track provided for the slider 24 in the housing.

A similar device is disclosed in WO 2007/022395. In this device, a catheter outer sheath 262 is rigidly attached to a slider block 624 in the device housing. A belt 670 is provided, connected to the slider block 624 and passing around a proximal idle pulley 638 to be connected at its other end to a take-up pulley 656. Take-up pulley 656 may be rotated by an operator via a knob 640, 650, in order to wind the belt 670 onto the reel 656. As the belt is wound onto the reel, the hub 624 is retracted so as to withdraw the outer sheath 262. As the belt is wound onto the take-up pulley 656, the winding diameter of the pulley increases, thereby reducing the mechanical advantage afforded, simultaneously increasing the degree of retraction for a given rotation of the knobs 640, 650. A lock 646 may be provided so as to inhibit rotation of the knobs 640, 650 during shipping, although explanation of the operation of this lock is not given. The length of a retraction stroke of the device is again limited by the length of the track provided for sliding the proximal hub 624 within the device housing.

Several sheath retraction devices are disclosed in WO 2005/039448 A1. In the first illustrated embodiment of FIGS. 1 to 5, a wire 160 is provided, connected to the outer tube (sheath) 130. The wire is connected to a cam 190 in the device housing. The cam is coupled to a thumbwheel 180, which may be rotated by a medical practitioner when using the device. Rotation of the thumbwheel 180 causes the wire 160 to be wound onto the surface 192 of the cam 190 so as to withdraw the outer tube 130 proximally with respect to the catheter inner tube 140. Since the radius of the cam 190 increases around the cam's surface 192, the mechanical advantage provided for retracting the outer tube 130 decreases as the wheel 180 rotates, with the degree of retraction for a given amount of rotation of the thumbwheel 180 correspondingly increasing as the thumbwheel 180 rotates. The device of WO 2005/039448 is configured to achieve only a single rotation of the thumbwheel 180, thereby limiting the retraction stroke to a distance equal to the circumference of the cam outer surface 192.

For minimally invasive surgical procedures utilizing a catheter, as with any surgical procedure, hygiene is of paramount importance. Regardless of the level of trauma caused by the surgical operation, the risks of infection must be minimized or neutralised, to ensure and aid a patient's recovery. For this reason, surgical catheter devices are usually provided with a control device already attached to the catheter's proximal end, and, in the case of a stent delivery catheter, with the stent already loaded in the catheter distal end. The surgical apparatus is typically packaged in sterile packaging, ready for use when first exposed from the packaging.

Because a surgical catheter is typically several times longer than the associated control device, the catheter is normally packaged in a rolled, folded or bent configuration, rather than in a fully elongated, straight configuration. This is enabled by the inherent flexibility of such catheters. In order to use the surgical apparatus, the catheter is straightened for insertion translumninally into a patient, and is then guided to the treatment site within a patient's vasculature. Typically, a guide-wire is provided, along which the catheter is run, to bring the distal end of the catheter to the treatment location.

Both when folding and unfolding the catheter for packaging and distribution purposes, and also when running the catheter along a guide-wire to follow a tortuous passage way, localized relative motion necessarily occurs between the catheter and the sheath. In particular, the sheath is necessary relatively inextensible in the lengthwise axial direction, to enable controlled withdrawal in use. The catheter material is typically moderately elastic, so as to provide the necessary lateral flexibility, with rigidity provided by a coil spring or other reinforcing support member as described above. As the catheter bends and flexes, localized movement between the catheter and sheath can thus occur. So that this will not result in accidental premature retraction of the sheath, the sheath distal end may be formed to extend over the end of the catheter to form an atraumatic distal tip. In other known catheters, an atraumatic tip may simply be provided on the distal end of the catheter. An element of slack or flexibility is also typically provided in the sheath retraction wire, which is itself substantially inextensible, so as to accommodate relative motion of the sheath proximal end with respect of the catheter.

The overall effect of the tolerances provided to allow such flexibility and relative motion means that when the operator comes to retract the sheath, the initial stages of sheath retraction may not deliver a controlled or expected degree of motion in the sheath, as the slack is taken up. In particular, at the initial stages of stent deployment, it is essential to have full control of the positioning and placement of the stent at the distal end of the surgical catheter device, to prevent accidental movement of the stent relative to the treatment site, which could result in an unintentional patient trauma.

There is also typically some inherent lengthwise compressive flexibility in the catheter, and some lengthwise tensile flexibility in the sheath, upon initial delivery to the treatment site, before any residual compressibility or extensibility can be taken up by proximal lengthwise tensioning of the sheath wire to place the catheter under compression along the catheter length. This initial catheter compression can produce undesirable preliminary motion at the catheter distal end as the sheath retraction device is first actuated.

Whilst prior art devices including two or more separate retraction mechanisms for delivering different mechanical advantages have been provided, so as to achieve slow initial sheath withdrawal for accurate placement of the stent distal end and fast subsequent sheath withdrawal for quickly releasing the stent when placed, no device has yet been produced to specifically account for the inherent residual tolerances and material resilience of the surgical catheter construction. It would therefore be desirable to provide a sheath withdrawal device constructed and arranged to accommodate specifically such residual tolerances and the material resilience of the surgical catheter construction.

It would also be desirable to provide indication to the user of such devices of when the sheath has been fully retracted, to ensure proper and accurate stent release and to indicate when the catheter may be retracted from the patient.

WO 20061104143 A1 discloses a body organ expansion instrument 1 having a tubular member 5 capable of sliding in a proximal direction at the distal end of a distal tube 2. A pulling wire 6 is attached at the proximal end to a winding shaft portion 63 which retracts the wire 6 by winding wire 6 thereon. A linear member 71 is also provided to be wound onto shaft portion 63 also. The linear member is fed out from a bobbin 73, around which it is initially wound, as the linear member 71 is wound onto shaft portion 63. When linear member 71 is all fed out, the bobbin 73 is nonrotatable, thereby making rotational roller 61, which winds the shaft portion 63 to retract wire 6, incapable of further rotating. The end 71a of the linear member 71 is inserted into a slit 72 to be held on the shaft portion 63. The shaft portion 63 is, however, provided only with a single slit 72, and the length of linear member 71 must therefore be made in accordance with the length of the specific stent to be held by tubular member 5 at the distal end of distal tube 2.

It would be desirable to provide means whereby the same device, or devices having substantially identical construction, can be adapted for retracting the sheath by amounts corresponding to different lengths of stents to be released, and to provide indication of full and proper sheath retraction appropriate to the length of each stent being released.

SUMMARY OF THE INVENTION

According to a first aspect of the present invention, there is provided a device for moving an elongate member relative to an elongate body through which it at least partially extends, the device comprising a housing connectable to the elongate body; a mover associated with the housing and connectable to the elongate member for moving the elongate member relative to the housing and relative to a connected elongate body; and a pre-mover for adjusting an elongate member connected to the mover relative to an elongate body connected to the housing in preparation for moving the elongate member with the mover.

In preferred embodiments, the pre-mover resists movement of the elongate member by the mover prior to adjusting the elongate member.

In further preferred embodiments, the pre-mover is configured for adjusting the elongate member relative to the elongate body to reduce slack between the elongate member and the elongate body to ensure direct subsequent relative movement therebetween by the mover.

In yet further preferred embodiments, the pre-mover is configured to adjust the mover relative to the housing so as to relatively adjust the elongate member and the elongate body respectively connected thereto.

In even further preferred embodiments, the pre-mover is configured to effect a predetermined relative adjustment between the elongate member and the elongate body.

In yet even further preferred embodiments, the pre-mover is configured to become inoperable following adjustment of the elongate member.

In more preferred embodiments, the mover is operable to move the elongate member only in a first direction relative to the elongate body.

In yet more preferred embodiments, the device is configured for the mover to move the elongate member towards the housing relative to the elongate body, which is fixedly connected to the housing.

In even more preferred embodiments, the device further comprises an accumulator, by which the elongate member is connectable to the mover and a portion of the elongate member is formed as an accumulation in the housing.

In yet even more preferred embodiments, the device further comprises a limiter for limiting the extent of movement of the elongate member relative to the elongate body. In such embodiments, the limiter may comprise a band of substantially inextensible material which is connected at one end to, and is wound on, a spool which is mounted to the housing, the band being connected at the other end to a winding member of the mover onto which the band is wound from the spool as the mover moves the elongate member, thereby permitting movement of the mover until the band is fully unwound from the spool and thereafter preventing further movement of the elongate member by the mover.

In still further preferred embodiments, the elongate body comprises a surgical catheter configured for insertion into a bodily lumen, and which includes a sheath which surrounds at least a distal end portion of the catheter; the elongate member is a wire for moving the sheath relative to the catheter; and the housing is connectable to a proximal end of the catheter.

In yet still further preferred embodiments, the mover comprises a take-up reel mounted to rotate relative to the housing onto which the elongate member is wound to effect movement thereof.

In still even further preferred embodiments, the mover includes an actuator by which a user of the device may actuate the mover to move the elongate member. In such embodiments, the actuator may include a trigger pivotally mounted to the housing to pivot between an extended position and a depressed position and configured to rotate a trigger gear by which to actuate the mover. More preferably, the trigger may include a planetary gear by which to rotate the trigger gear. Even more preferably, the trigger gear is coupled to a drive shaft of the mover by a one-way clutch so as to enable the trigger gear to rotate the drive shaft when depressed towards the depressed position but preventing the trigger gear from rotating the drive shaft when returned towards the extended position, the trigger being biased towards the extended position.

In still more preferred embodiments, the mover includes: a toothed gear mounted to rotate relative to the housing; and a leaf spring fixedly mounted to the housing and arranged so that one end thereof engages with the teeth of the toothed gear at a non-radial angle of incidence to the gear, the leaf spring being resiliently flexible to disengage from the gear teeth and allow rotation of the toothed gear in one direction and to engage the gear teeth and substantially resist rotation of the gear in the other direction, so as to effect a ratchet arrangement to permit actuation of the mover to move the elongate member only in one direction relative to the elongate body.

In yet still more preferred embodiments, the pre-mover includes a rack gear configured to engage initially with a pinion gear of the mover, so that adjustment of the elongate member relative to the elongate body is effected by actuation of the rack gear to rotate the pinion gear of the mover.

In still even more preferred embodiments, the rack gear is mounted to a slider arm which is connected at one end to a button which is mounted to slide relative to the housing and is arranged to be actuated by a user to effect actuation of the rack gear.

In yet still even further embodiments, the housing forms a sealed unit in which the mover and pre-mover are mounted to be actuated by a user. In such embodiments, preferably the housing is sized and configured, and an actuator of the mover and of the pre-mover are arranged, so as to facilitate operation of the device with a single hand by a user.

According to a second aspect of the present invention, there is provided a device for moving an elongate member by a predetermined distance relative to an elongate body through which it at least partially extends, thereby to release a stent at the distal end of the elongate body, the device comprising: a take-up reel onto which the elongate member is wound when it is moved; and a limiter that is configured to limit further rotation of the take-up reel after a length of the elongate member has been taken up on the reel to move the elongate member said pre-determined distance, wherein the limiter comprises a tethered line, which is configured to be progressively consumed when the take-up reel is rotated until the tethered line anchors the take-up reel against further rotation, one end of the tethered line being provided with a line connector by which it may be attached to a limiter reel on which it is to be taken up to be consumed, and wherein the limiter reel is provided with plural reel connectors to which the line connector may be connected to attach the tethered line to the limiter reel.

In preferred embodiments, the line connector is a male connector and the reel connectors are female connectors into which the male connectors can be connected. More preferably, the line connector is a ball or cylinder joined onto the end of the tethered line. Yet more preferably, the tethered line has a total length, of which a consumable length corresponding to the length of said elongate member to be taken up may form all or a portion, the limiter being adjustable to set the consumable length to correspond to the length of said elongate member to be taken up prior to use of the device for effecting the predetermined relative movement between the elongate body and the elongate member, preferably during manufacture-and-assembly of the device.

According to a third aspect of the present invention, there is provided a device for moving an elongate member by a predetermined distance relative to an elongate body through which it at least partially extends, thereby to release a stent at the distal end of the elongate body, the device comprising: a take-up reel onto which the elongate member is wound when it is moved; and a limiter that is configured to limit further rotation of the take-up reel after a length of the elongate member has been taken up on the reel to move the elongate member said pre-determined distance, wherein the limiter comprises a tethered line, which is configured to be progressively consumed when the take-up reel is rotated until the tethered line anchors the take-up reel against further rotation, wherein the tethered line to be consumed has a consumable length corresponding to the length of said elongate member to be taken up, and wherein (i) a plurality of tether lines are provided having different respective consumable lengths, from which the tethered line to be consumed is selected having a consumable length which corresponds to the length of said elongate member to be taken up, or (ii) a tether line is provided having reference markings along its length indicating different consumable lengths corresponding to different lengths of said elongate member which can be taken up, the consumable length being set by the tether line being consumed, prior to moving the elongate member, up to the reference marking which indicates a remaining consumable length corresponding to the length of said elongate member to be taken up.

Preferably, the tethered line is consumed by being taken up on a limiter reel. More preferably, the tethered line is carried on a tether spool, and is unspooled from the tether spool while being progressively consumed during rotation of the take-up reel.

In further preferred embodiments, the elongate body is a catheter and the elongate member IS a sheath refraction wire for proximally retracting a sheath that surrounds the abluminal surface of the stent to be released at the catheter distal end.

The present invention also provides a surgical apparatus including a device as set forth above and having an elongate body connected to the housing and an elongate member connected to the mover.

In preferred embodiments, the surgical apparatus further includes a stent carried by the elongate body for delivery to a target site of a patient and releasable from the elongate body at the target site by movement of the elongate member relative to the elongate body. Preferably, the stent is a self-expanding stent suitable to be implanted at a treatment location in a bodily lumen, and the device is configured to effect a pre-movement adjustment of the elongate member relative to the elongate body, said adjustment including a preliminary movement of the elongate member relative to the elongate body insufficient to release any portion of said stent to an expanded diameter permitting circumferential engagement with the inner wall of the bodily lumen at the intended treatment location. More preferably, said preliminary movement is insufficient to release any portion of said stent from the elongate body. Most preferably the stent is a self-expanding stent, and the device is configured to effect a pre-movement adjustment of the elongate member relative to the elongate body, said adjustment including a preliminary movement of the elongate member relative to the elongate body insufficient to release any portion of the stent to an expanded diameter of more than 110% of the stent unreleased diameter, preferably 105% or less of the stent unreleased diameter.

According to a fourth aspect of the present invention, there is provided a stent delivery device, comprising: a housing connectable to an elongate body; a mover coupled to a housing and connected to an outer sheath disposed over a stent compressed about a distal end of the elongate body; and a pre-mover associated with the housing having a locked position engaging the mover and an unlocked position in which the mover is released, wherein movement of the pre-mover from the locked position to the unlocked position prepares the outer sheath for deployment of the stent.

According to a fifth aspect of the present invention, there is provided a stent delivery device, comprising: a take-up reel onto which a sheath retraction line is wound when an outer sheath which surrounds a compressed stent at a distal portion of the delivery device is retracted; and a limiter which limits the length of the sheath retraction line which may be taken up on the reel so as to limit retraction of the outer sheath, wherein the limiter comprises a limiter reel and a tethered line which is progressively consumed by the limiter reel when the take-up reel is rotated and which anchors the take-up reel against further rotation when fully consumed, one end of the tethered line being provided with a line connector attached to the limiter reel, and wherein the line connector is connected to one of plural reel connectors disposed around the limiter reel.

According to a sixth aspect of the present invention, there is provided a stent delivery device, comprising: a take-up reel onto which a sheath retraction line is wound when an outer sheath which surrounds a compressed stent at a distal portion of the delivery device is retracted; and a limiter which limits the length of the sheath retraction line which may be taken up on the reel so as to limit retraction of the outer sheath, wherein the limiter comprises a limiter reel and a tethered line connected to the limiter reel, which is progressively consumed by the limiter reel when the take-up reel is rotated, wherein the tethered line has a consumable length corresponding to the retraction limit of the outer sheath, and wherein (i) one or more further tether lines are provided having respective consumable lengths different from the length of the tethered line connected to the limiter reel, or (ii) the tether line connected to the limiter reel has reference markings along its length indicating different available consumable lengths, the consumable length which corresponds to the retraction limit of the outer sheath being indicated by one said reference marker.

Embodiments of the first and fourth aspects of the invention set forth above are able to provide adjustment prior to bulk actuation of the mover, ensuring that tolerances are accommodated and that motion between the mover and housing translates directly into proportional motion between the elongate member and elongate body, thereby improving control accuracy with the device.

In particular for stent delivery catheter embodiments, unexpected deflection at the catheter tip as the sheath retractor is first activated can be reduced or eliminated.

Furthermore, an effective locking mechanism may be achieved, with certain embodiments, to prevent premature or accidental actuation of the mover.

Preferred embodiments are also able to accommodate different stroke length requirements, as the stroke length need not be restricted by the length of the housing or its components.

Embodiments of the second, third, fifth and sixth aspects of the invention set forth above can indicate to the user of the device, when a stent at the elongate body distal end has been fully released, preventing premature catheter withdrawal or unnecessary further movement of the elongate member, and are readily adaptable to different lengths of stent which the devices may be employed to release.

BRIEF DESCRIPTION OF THE DRAWINGS

To enable a better understanding of the present invention, and to show how the same may be carried into effect, reference will now be made, by way of example only, to the accompanying drawings, in which: —

DETAILED DESCRIPTION

Figure 1:
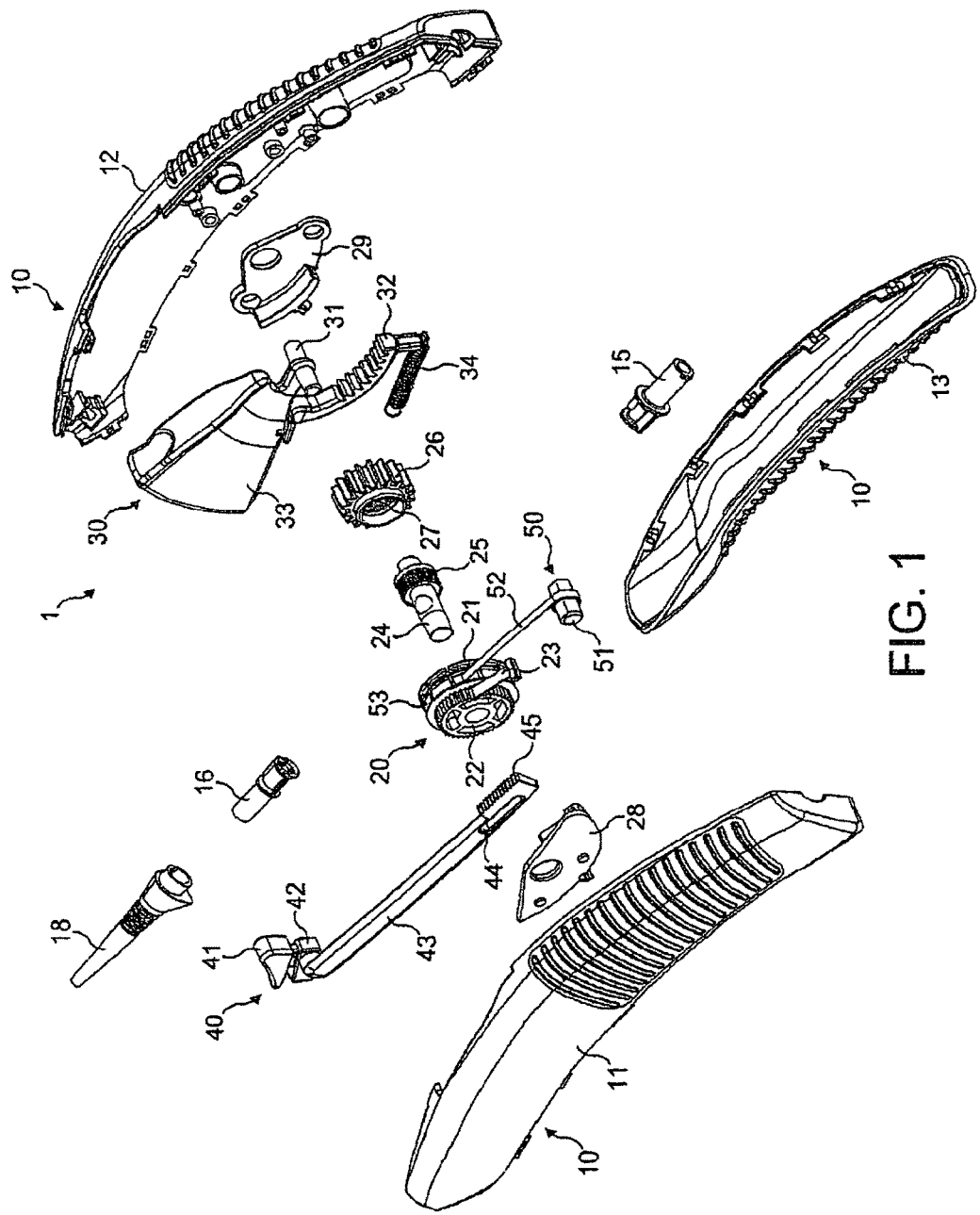
FIG. 1 shows an exploded perspective view of a catheter sheath retraction device as one embodiment of a device in accordance with the present invention, detailing the major internal and external component parts of the device.

The following detailed description is directed to a specific example of a catheter sheath retraction device, suitable for connection to the proximal end of a stent delivery catheter (elongate body) for retracting the catheter outer sheath, by virtue of a sheath retraction wire (elongate member), so as to expose a stent at the distal end of the catheter. It will be appreciated, however, that the utility of the disclosed device and the components of the actuator mechanism may find utility in alternative applications where actuation to achieve relative motion between two elongate components is required.

In the present specification, as is usual in this technical field, the term "proximal" refers to the direction or end of the device which, when in use, is generally towards the medical practitioner, and the term "distal" refers to the opposite sense, i.e. towards the patient or away from the medical practitioner.

The following description is made with reference to FIGS. 1 to 10 generally, and with reference to specific ones of the figures, where appropriate. The catheter sheath retraction device 1 generally includes a housing 10, a mover 20, a trigger 30, a pre-mover 40 and a limiter 50.

As shown in FIG. 1, the housing 10 is formed of a left housing 11, a right housing 12 and a lower housing 13, which together form an outer shell of the catheter sheath retraction device 1. The housing components will typically be formed of any suitable surgically compatible material to provide a substantially rigid outer shell. The housing is formed in an ergonomic shape, including ridged regions to provide grip for a user's hand. The housing is shaped so as to rest comfortably within one hand of a user, and to allow actuation of the trigger 30 with a single hand by a user. The device is furthermore configured to be substantially symmetric along its longitudinal axis, to permit facile use with either hand. The left 11, right 12 and lower 13 housing components are preferably molded separately before being joined together. The joints may be effected using suitable adhesive means, to form a sealed housing unit containing the components of the sheath retraction mechanism therein.

Preferably, the housing components 11, 12 and 13 are provided with resilient male/female connecting portions, which allow the housing components to be clipped together, as well as the joints being glued.

Figure 2:
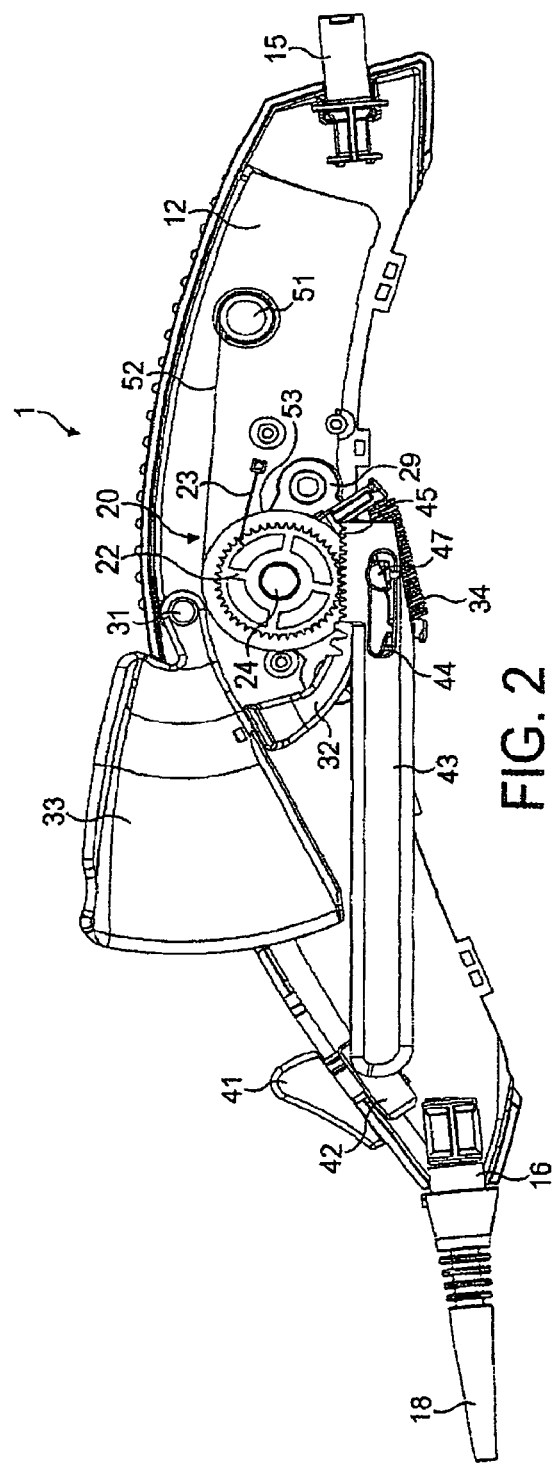
FIG. 2 shows a cross-sectional left-hand-side view of the catheter sheath retraction device of FIG. 1.

As is apparent from FIG. 2, the housing is provided with a rear connector 15 and a front connector 16, by which to provide a fluid-tight connection between the housing and a surgical catheter to be held therein. Connectors 15 and 16 preferably provide external access to the internal fluid passageways of the surgical catheter, for example, so as to introduce flushing fluid into the catheter prior to use, and to allow insertion and retraction of a guide wire through the catheter.

A conical nose or strain relief element 18 is provided at the distal end of the housing 10, to provide a rigid connection with the proximal end of a catheter. The strain relief element 18 enables the user to apply controlled forces to the surgical catheter, and relieves localised compression and bending forces at the catheter proximal end where it is connected to the housing 10. Front connector 16 and pusher 18 form the distal hub by which a reinforcing member of the surgical catheter is held in place relative to housing 10 to transfer compressive stresses to the housing.

When a surgical catheter is connected to the catheter sheath retraction device 1, the connector 16 is configured to allow a sheath pull wire to extend distally into the housing from the catheter. The sheath retraction device 1 is provided with a mover 20 for retracting the sheath pull wire proximally into the housing 10.

As described in WO 2005/053574 A2, the sheath pull wire can be connected to the sheath by, for example, first and second metal rings, one inside the other, and sandwiching the sheath so that one of the metal rings is inside the sheath annulus and the other is outside the sheath annulus. The inside metal ring would normally be welded, soldered or brazed to the distal end of the sheath pull wire (adhesives being generally disfavored in failure-critical applications in such stent delivery devices), while the outer metal ring can be swaged down onto the sheath to press the sheath onto the inner metal ring.

Figure 3:
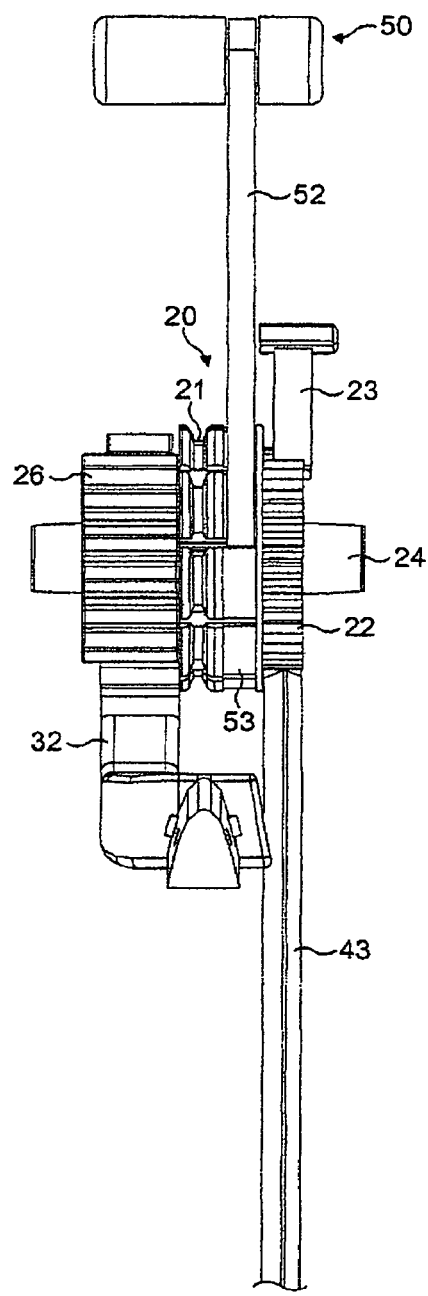
FIG. 3 shows a plan view of the main internal components forming the sheath retraction mechanism of the catheter sheath refraction device of FIG. 1 and FIG. 2.

As best seen in FIG. 3, the mover 20 is provided with a mover reel 21, onto which the sheath pull wire is to be wound as the mover reel 21 rotates. As can be seen, the mover reel 21 is formed with a circumferential V-shaped groove into which the sheath pull wire is received. The mover reel 21 is provided with slots or notches around its circumference, into which an end connector of the sheath pull wire can be received, to connect the sheath pull wire to the mover reel 21.

Although a sheath pull wire is mentioned as a specific, preferred example of an elongate member by which to retract the catheter sheath, it is of course possible in alternative configurations to utilize a band, chain or other flexible member to connect the sheath to the mover 20. As the mover reel 21 is rotated, the sheath pull wire is wound onto the mover reel 21, in the V-shaped groove, thereby retracting the sheath and accumulating the sheath pull wire on the mover reel 21. Accordingly, as the sheath wire is retracted into the housing and wound on the mover reel 21, the sheath is retracted towards the catheter proximal end, as the catheter itself is held in place by the housing 10 and strain relief element 18.

As shown in FIG. 3, in particular, the mover reel 21 is mounted on a mover shaft 24 along with a number of further components. To enable the mover shaft 24 to rotate in the center of the housing, it is mounted between a pair of left and right support frames 28 and 29, respectively. Holes are provided in support frames 28 and 29 to support the shaft 24, and to allow the shaft 24 to rotate substantially freely. Left and right support frames 28 and 29, respectively, are configured to be fixedly mounted in the respective left and right housing portions 11 and 12.

Figure 10:
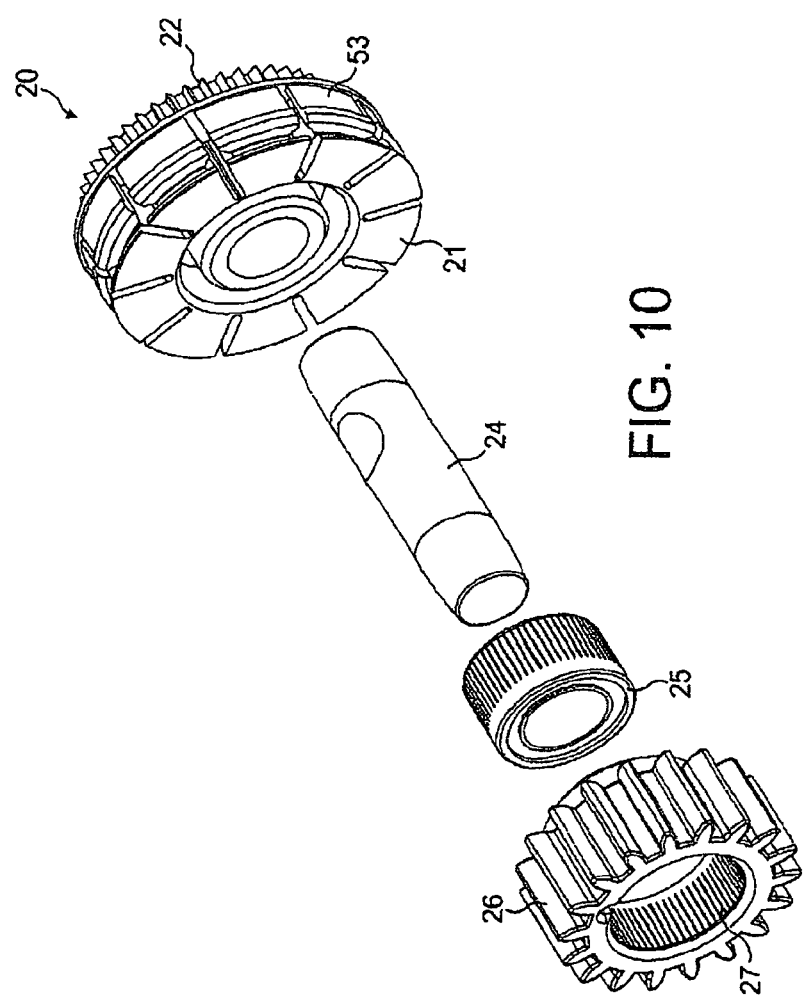
FIG. 10 shows an exploded perspective view of the main rotational shaft at the center of the catheter shaft retraction device of FIGS. 1 to 9, and the rotary components to be mounted thereto.

As shown in FIG. 3, the mover reel 21 and mover shaft 24 are provided, on the left side of the catheter sheath retraction device 1, with a mover toothed gear 22. Mover toothed gear 22 is rigidly coupled with the mover reel 21, either via the mover shaft 24, or through being constructed as a unitary component therewith. In the present example, as shown in FIG. 10, the mover reel 21 and mover toothed gear 22 are formed as a unitary component, along with a limiter reel 53, to be described further below. The mover reel 21 and toothed gear 22 are directly coupled to the shaft 24, to rotate together therewith.

Figure 4:
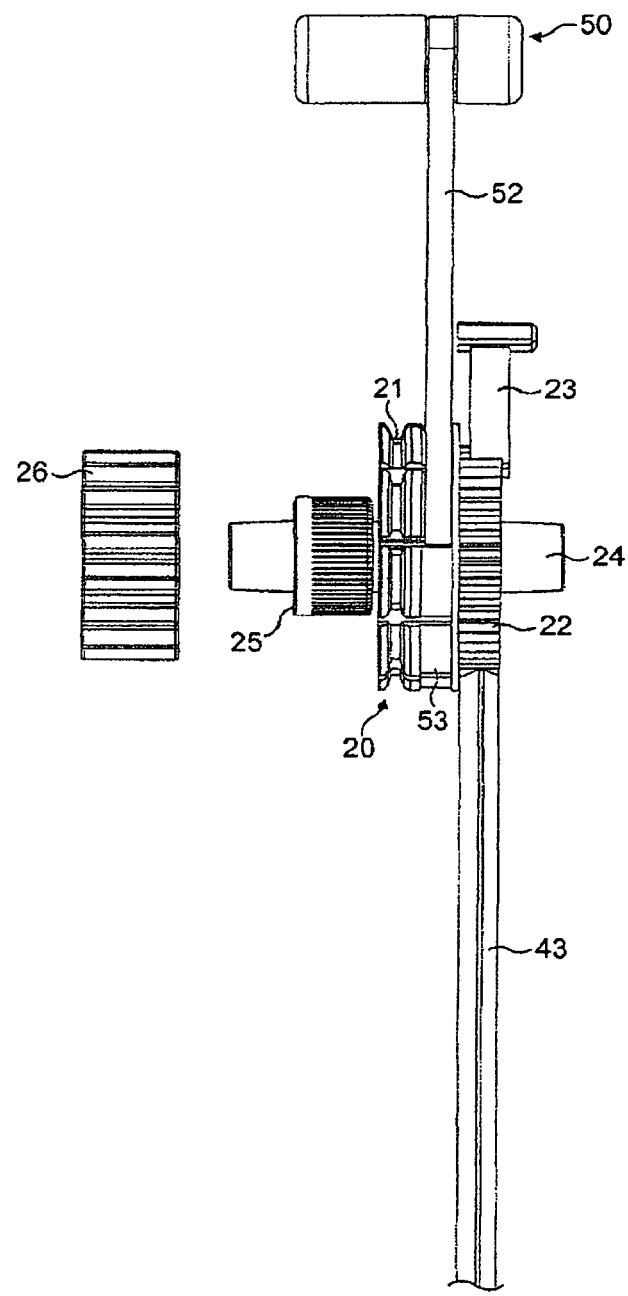
FIG. 4 shows a similar plan view of the components of FIG. 3, with the planetary gear omitted, indicating how a trigger gear is connected to the main shaft of the sheath retraction mechanism by virtue of a one-way clutch.
Figure 5:
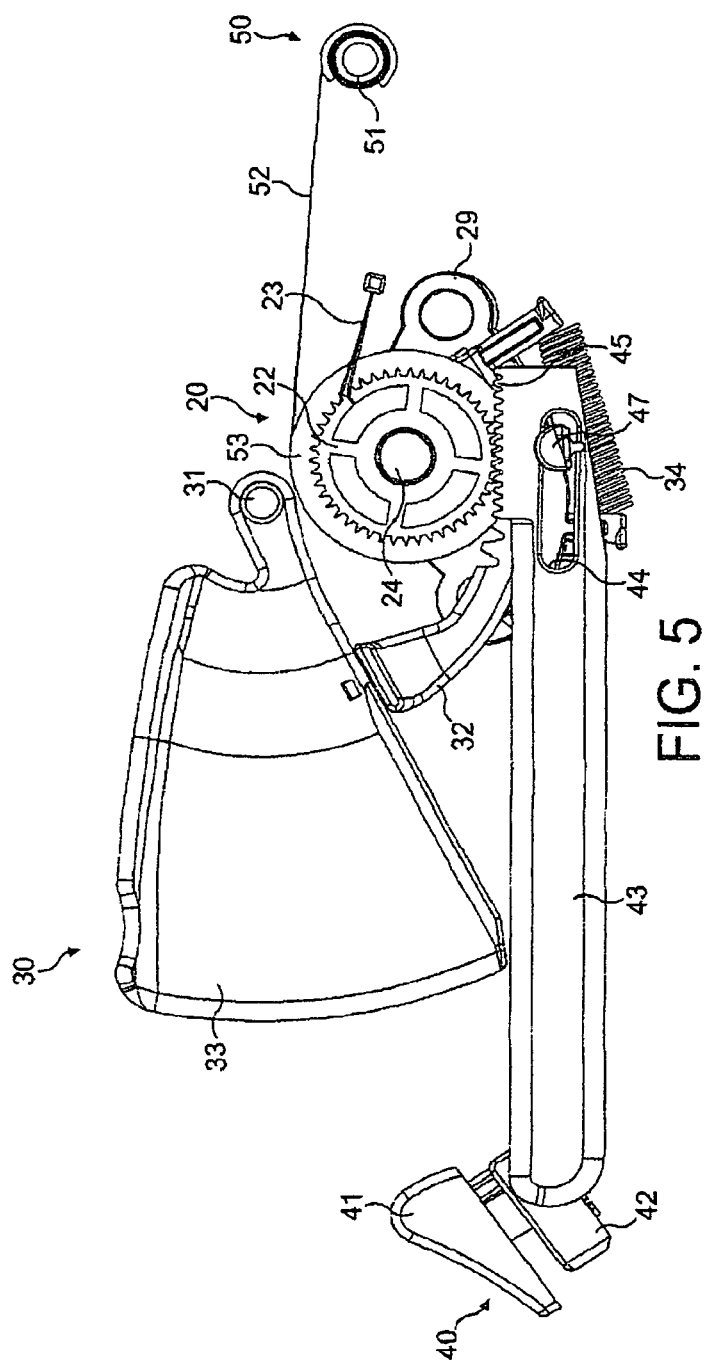
FIG. 5 shows a left-hand-side view of the working components of the retraction mechanism of the catheter sheath retraction device of FIGS. 1 to 4.

The mover shaft 24 is further provided with a trigger gear 26. As shown in FIG. 4, trigger gear 26 is not coupled directly to the mover shaft 24, but is engaged therewith via a one-way clutch arrangement. Specifically, a one-way clutch 25 is provided on mover shaft 24. Clutch 25 is a standard component for providing a rigid connection for transmitting forces from the trigger gear 26 to the mover shaft 24 in a driving direction, and for allowing the trigger gear 26 to rotate freely of the mover shaft 24 in the opposite direction.

As best seen in FIG. 10, for example, the trigger gear 26 is formed with a cylindrical through-hole 27 into which the one-way clutch 25 is press-fitted. Grooves in the one-way clutch 25 outer surface deform the inner surface of through-hole 27 to fixedly engage the clutch 25 in the trigger gear 26.

Figure 6:
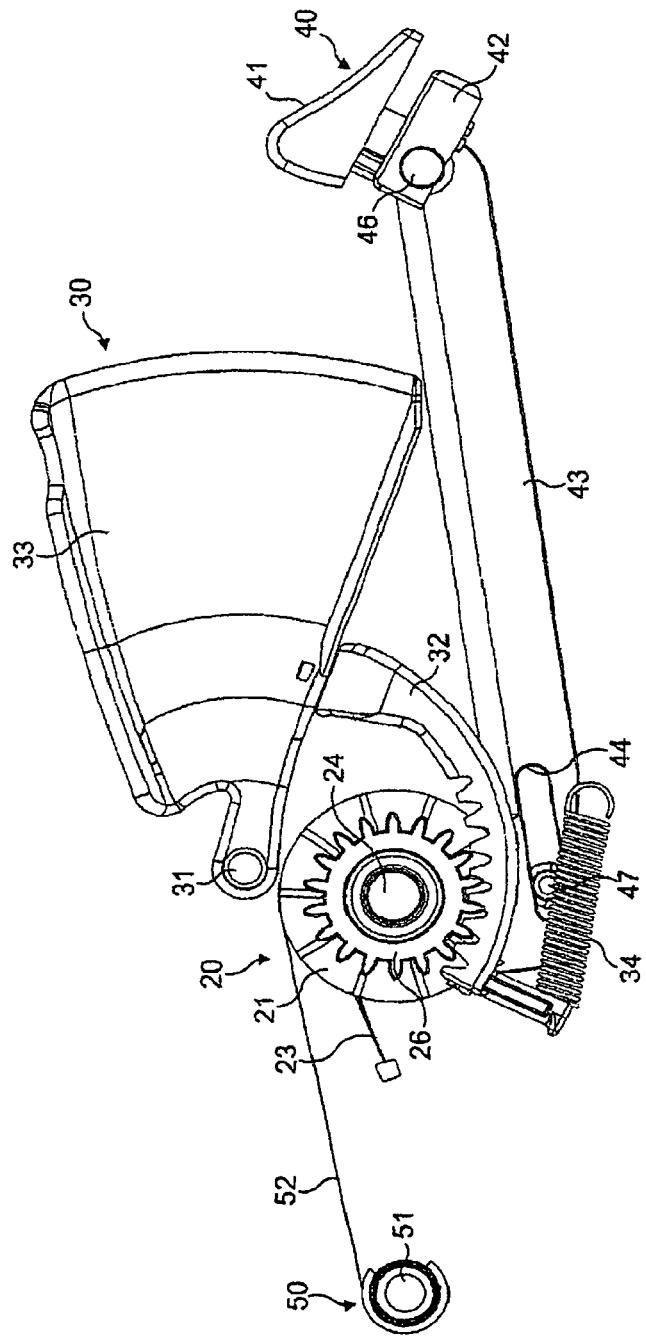
FIG. 6 shows a right-hand-side view of the retraction mechanism of the catheter sheath retraction device of FIGS. 1 to 5.
Figure 7:
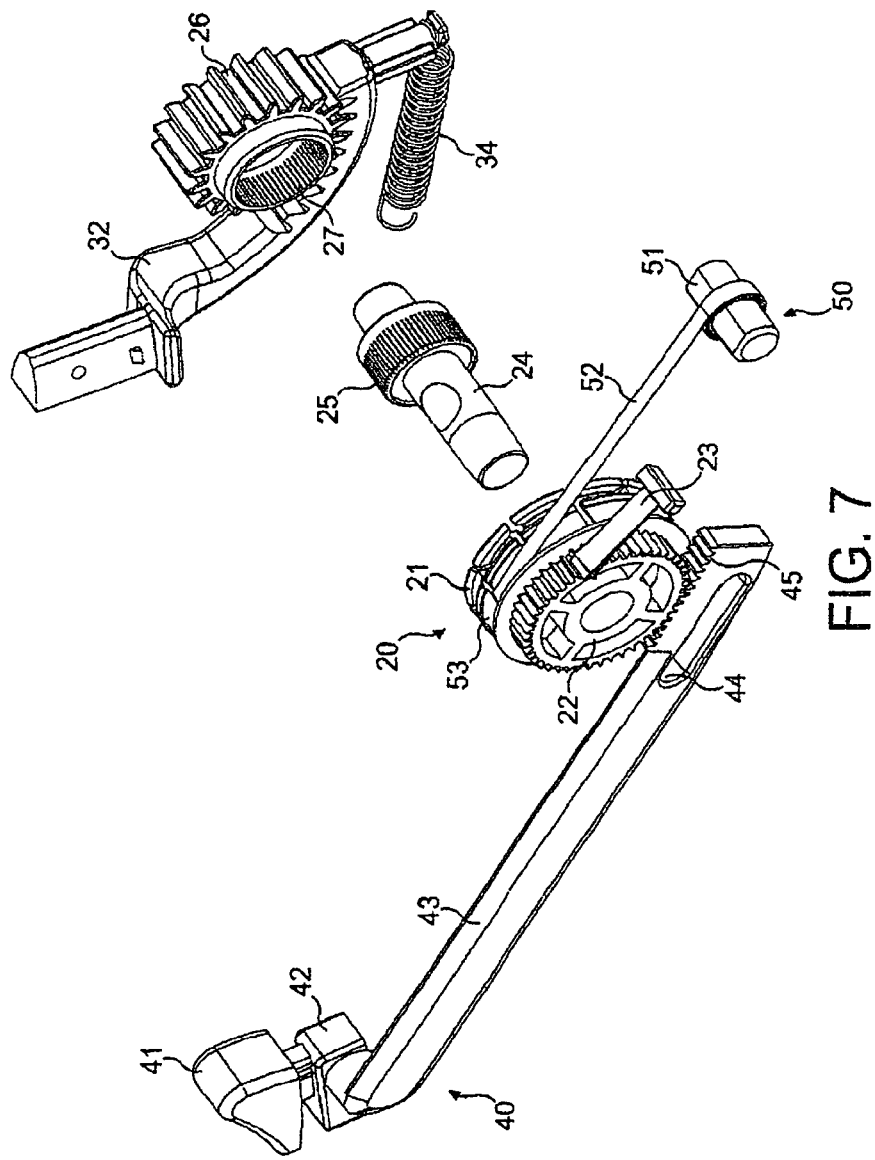
FIG. 7 shows a perspective exploded view of the components of FIGS. 5 and 6.
Figure 8:
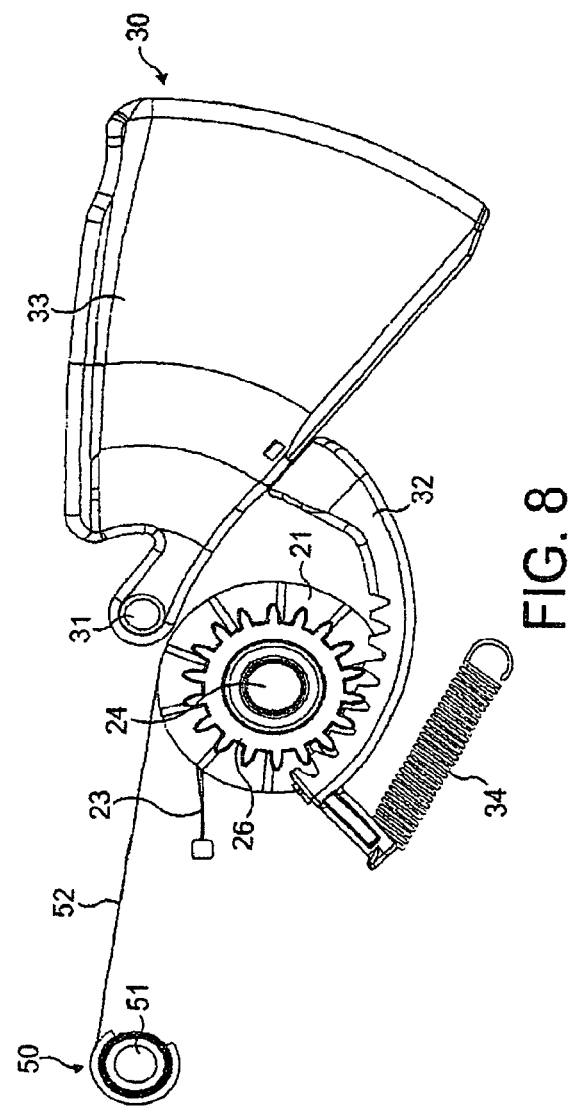
FIG. 8 shows a detailed view of the trigger actuator components of the catheter sheath retraction device of FIGS. 1 to 7.

The one-way clutch 25 is configured to engage with mover shaft 24 so as to transmit drive from the trigger gear 26 to the mover shaft 24 in a first, winding direction (anti-clockwise as shown in FIGS. 1, 2, 5, 7 and 9 and clockwise as shown in FIGS. 6, 8 and 10). When rotated in this winding direction, the internal components of one-way clutch 25 engage mover shaft 24 to transmit drive from the trigger gear 26 to the mover shaft 24. When the trigger gear 26 is rotated in the opposite sense, the internal components of one-way clutch 25 are configured to disengage from mover shaft 24, allowing the trigger gear 26 to rotate separately from the mover shaft 24.

Accordingly, the trigger gear 26 may be rotated so as to cause the mover reel 21 to rotate in a first, winding direction, thereby to wind the sheath pull wire onto the mover reel 21. The trigger gear 26 will not, however, cause the mover reel 21 to rotate in the reverse direction, thereby unwinding the sheath pull wire from the mover reel 21.

Of course, in practice, the one-way clutch 25 is capable of transmitting some torque to the mover shaft 24, even in the non-winding direction. To prevent these unavoidable minimal forces from transmitting drive from the trigger gear 26 to the mover shaft 24 in the reverse direction, the catheter sheath retraction device 1 is provided with a leaf spring 23, as shown in FIGS. 1 and 3. The leaf spring 23 is mounted to the housing 10, in the present example to the left housing 11, to be rigidly and fixedly supported at one end thereof. The leaf spring 23 is mounted so that the other, free end thereof is in contact with the teeth of the mover toothed gear 22, and projects into the toothed region at an angle oblique to the radial direction of the toothed gear 22. By this arrangement, the leaf spring 23 is configured to allow the toothed gear 22 to rotate in a first direction (anti-clockwise, as shown in FIGS. 1, 2, 5, 7 and 9), due to the teeth of the fixed gear 22 deflecting the resilient leaf spring 23 radially outwardly with respect to the toothed gear 22 so as to disengage it from the teeth as the toothed gear 22 rotates.

Figure 9:
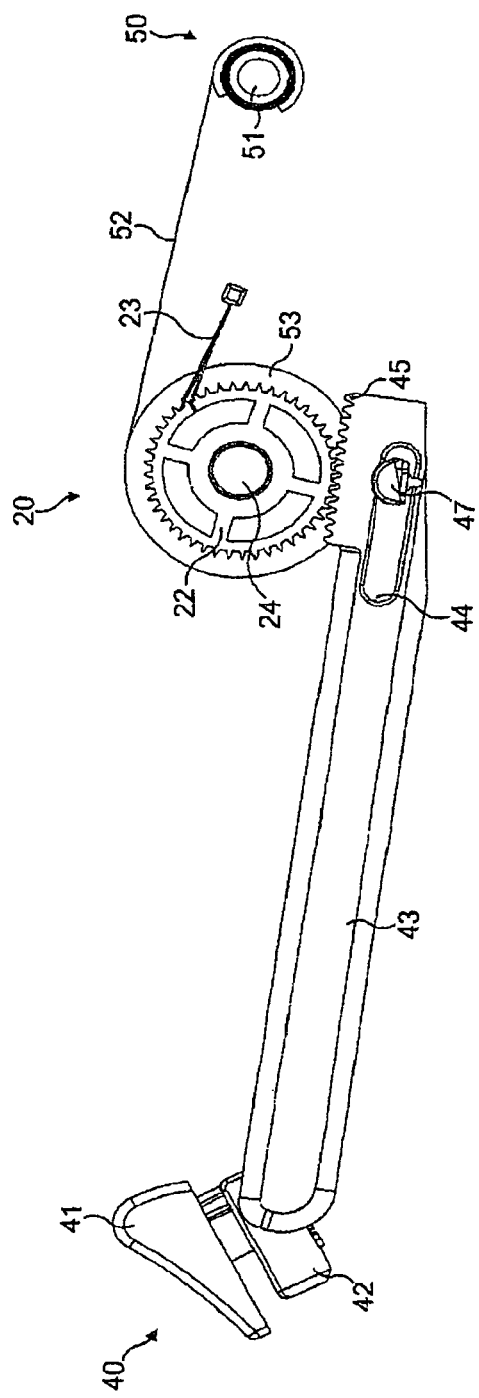
FIG. 9 shows a view of the components of a pre-mover assembly of the catheter sheath retraction device of FIGS. 1 to 8.

As best seen in FIG. 9, however, when the toothed gear 22 attempts to rotate in the opposite sense (clockwise, as shown in FIG. 9), the oblique interface of the free end of the leaf spring 23 with the teeth of the toothed gear 22 causes the teeth of the toothed gear 22 to engage the leaf spring 23 in a longitudinally compressive sense, rather than in a direction transverse to the leaf spring 23 long axis. Accordingly, the leaf spring 23 is not caused to deflect radially outwardly, and instead engages positively with the teeth of the toothed gear 22, preventing rotation in the reverse, non-winding direction.

Accordingly, by the combined operation of the one-way clutch 25 and the ratchet effect produced by the leaf spring 23, a drive system is configured for providing uni-directional drive in the winding direction of the mover reel 21 via the mover shaft 24. Furthermore, the degree of rotation of the mover shaft 24 imparted by rotation of the trigger gear 26 in the winding direction is not disturbed by subsequent reverse rotation of the trigger gear 26, such as when the trigger 30 is released.

As shown in detail in FIGS. 6, 7 and 8, the catheter sheath retraction device 1 is provided with a trigger 30. Trigger 30 includes a user-engagement portion 33 which projects through an opening in the housing 10 for engagement and manipulation by a user of the catheter sheath retraction device 1. The trigger 30 is pivotally mounted in the housing 10 by a trigger pivot shaft 31, about which the trigger 30 prescribes a part-circular, arcuate path. The trigger pivot shaft 31 may be mounted in the housing 10 either in further holes provided in the left and right support frames 28 and 29, or, as in the present example, directly mounted in a shaft receiving hole in each of the left and right housings 11 and 12.

The trigger user engagement portion 33 is connected to a planetary gear 32, which is also constrained to follow a part-circular arcuate path as the trigger 30 is depressed by a user pressing on the trigger user engagement portion 33. The trigger 30 is mounted in the housing 10 so that the planetary gear 32 engages with the trigger gear 26 mounted on the mover shaft 24, as seen in FIGS. 3 and 8, for example. Accordingly, each depression of the trigger 30 rotates the trigger gear 26 in the winding direction, so as to wind the mover reel 21 by a certain amount. The trigger 30 is also provided with a trigger spring 34 for biasing the trigger from a fully depressed position to an extended position fully projected, within the trigger's arc of travel, from the housing 10. After the trigger 30 has been depressed from the extended position to the depressed position, and then released, the spring 34 returns the trigger 30 to the extended position through its biasing action. Although a coil spring is specifically exemplified in the illustrated embodiment, any suitable biasing means may be used to return the trigger to the extended position after each depression. This trigger return motion causes the trigger gear 26 to reverse in the opposite sense to the winding direction. However, as noted above, no drive is transmitted to the mover reel 21 in the unwinding direction, by virtue of the one-way clutch 25. Again, as noted, any minimal forces attempting to rotate the mover shaft in the unwinding direction are resisted by the leaf spring 23 engaging with the teeth of the fixed gear 22.

In this way, a plurality of sequential depressions of the trigger 30 can be used to fully retract the catheter sheath by winding the sheath pull wire on the mover reel 21. Each full depression of the trigger 30 will retract the sheath pull wire by a substantially constant pre-determined amount. Within practical limits, the trigger 30 can be utilized to wind up a sheath pull wire of substantially any length, unconstrained by the physical length of the housing 10. Accordingly, the same housing 10 and retraction mechanism, comprising the mover 20 and trigger 30, can be utilized to retract a catheter sheath by substantially any given length, without needing to modify the components of the housing 10, mover 20 or trigger 30.

The distance by which any sheath must be retracted is essentially the same as the length of the stent to be deployed, typically 20 mm to 200 mm. The sheath may run along substantially the entire length of the catheter, which would have a typical length from 60 cm to 135 cm, although catheter lengths up to 200 cm are also known, for endoscopic applications and such like. Alternative sheath designs include a sheath only along the distal portion of the catheter delivery system, in which case the length of such a sheath would normally be from 100 mm to 400 mm, suitable for use with the existing standard lengths of stents to be deployed.

On the other hand, it is preferable for the operator of the catheter sheath retraction device to have an indication of when the sheath at the distal portion of the catheter has been fully retracted, such that a stent mounted at the distal end of the catheter has been released. To this end, a limiter 50 is provided. Limiter 50 is mounted, in the present example, in a proximal portion of the housing 10. The limiter includes a tethered line, which is realized in this example by a spool 51 on which a band 52 is wound. In a preferred embodiment, the limiter band 52 is provided of a fixed length, with reference markings to indicate particular positions along the band 52 which each denote an amount by which the band 52 is to be unwound (and rolled-up onto limiter reel 53). The amount provided by each marker provides for a consumable length of the band 52 remaining spooled on the limiter spool 51 which corresponds to (but is not necessarily equal to) the distance by which a particular sheath to be retracted by the catheter sheath retraction device 1 is to be retracted. During manufacture or set-up of the catheter sheath retraction device 1, the band 52 is unspoiled from spool 51 and around onto limiter reel 53 until the marker corresponding to the required sheath retraction distance is revealed, leaving the spooled portion of band 52 with a remaining consumable length corresponding to said required sheath retraction distance.

In practice, there are twelve standard lengths of stent (there are twelve stent lengths commonly adopted within the medical devices industry, as an informal standard, ranging from 20 mm to 200 mm). Accordingly, each band 52 may be provided with eleven or twelve such markers, allowing accurate adjustment of the band 52 consumable length to any one of the twelve standard lengths. Stents up to 300 mm in length are also contemplated, and bands of appropriate length having any number of suitable markers may of course be provided to accommodate any such other stent length. Most preferably, the adjustment of the band 52 consumable length is undertaken during manufacture and assembly of the catheter sheath retraction device 52. As an alternative, a specific limiter band 52 may be selected which has a particular length, in particular including a consumable portion having a length corresponding (but not necessarily equal) to the distance by which a particular sheath is to be retracted by the catheter sheath retraction device 1.

The unspooled free end of the limiter band 52 is provided with a connector, such as a ball or cylinder welded or otherwise joined onto the end of the band 52, for example. The band 52 is substantially inextensible in its lengthwise direction. The free end of the limiter band 52 provided with the connector is attached to the limiter reel 53, which is provided in the present example mounted on the shaft 24 between the mover reel 21 and the toothed gear 22.

As visible in FIGS. 3, 4, 6, 7, 8 and 10, the limiter reel 53 is provided with one or more female connector portions around its circumference, into which the connector on the free end of the limiter band 52 may be inserted and retained. Preferably, the limiter reel 53 is provided with plural female connector portions, which enable the free end of the limiter band 52 to be attached at a variety of positions around the limiter reel. This enables the mover reel 21 to be rotated to a suitable initial position in dependence on the initial winding-on of the sheath pull wire onto the mover reel 21, and for connecting the limiter band to the limiter reel to provide the correct consumable length independently of the rotational position of the mover reel 21. The length of the limiter band to be consumed can therefore be adjusted with greater freedom, unconstrained by the position of the sheath pull wire.

In operation of the catheter sheath retraction device, as the mover shaft 24 rotates to wind the sheath pull wire onto the mover reel 21, the limiter band 52 is similarly wound onto the limiter reel 53, as it is unspooled from the spool 51. When the pre-determined length of the limiter band 52 has been unspooled from the spool 51 and wound on the limiter reel 53, the inextensible limiter band 52 prevents further rotation of the limiter reel 53, and consequently prevents further rotation of the mover shaft 24 and mover reel 21. This indicates to the user that the catheter sheath retraction device 1 has fully retracted the catheter sheath.

Accordingly, by simply adjusting the consumable length of limiter band 52 during manufacture or set-up of the retraction device, or by substituting the limiter band 52, according to the length of sheath to be refracted, the further components of the catheter sheath retraction device 1 can be left unaltered, regardless of the length of the catheter sheath to be retracted, thereby rendering identical (or virtually identical) ones of the device applicable to numerous sheath withdrawal applications with only this minor modification.

Turning now to FIG. 9, in particular, a pre-mover 40 of the catheter sheath retraction device 1 will be described. The pre-mover 40 is preferably a separate and distinct mechanism from any actuator device, such as trigger 30, for effecting retraction of the sheath, and is dissimilar in operation from incremental or bulk retraction actuators known in the prior art.

The illustrated pre-mover 40 includes a slider arm 43 provided with a slider arm groove 44 extending partially along the length thereof. Slider groove 44 is mounted on a slider pin 47 provided in the housing 10. Slider pin 47 may be formed as part of the left housing 11, or may form part of the left support frame 28. Slider arm 43 is thus constrained to move so that the slider groove 44 travels along slider pin 47.

The slider arm 43 is provided at its proximal end with a pre-mover rack gear 45. Rack gear 45 is configured to engage with the mover toothed gear 22, so that movements of the slider arm 43 in the proximal direction (in the right-hand direction as shown in FIG. 9) will cause the rack gear 45 to rotate the toothed gear 22 in the winding direction (anticlockwise in FIG. 9).

The pre-mover 40 is provided at the distal end with a pre-mover finger button 41, which is mounted on a pre-mover button slider 42. The pre-mover button slider 42 is pivotally connected to the distal end of the slider arm 43, mounted on a pivot shaft 46 of the slider arm 43 (see FIG. 6).

The pre-mover button slider 42 is mounted in a track provided in the housing 10, as shown in FIGS. 1 and 2. The button slider 42 is slidable along the track in the housing between a distal, locking position and a proximal release position. The pre-mover finger button 41 is configured to project outside the housing 10 when the button slider 42 is mounted in the track of the housing, as shown in FIG. 2, to enable manipulation by a user of the catheter sheath retraction device 1. The finger button 41 is configured for retraction by a user's single digit in the proximal direction.

As visible in FIG. 1, notches or dimples may be provided along the track in which the button slider 42 is mounted. In particular, a first notch, or pair of notches, is provided near to the distal end of the track and a second notch, or pair of notches, is provided near to the proximal end of the track. These notches provide a tactile indication to a user of the catheter sheath retraction device 1 to indicate, firstly, when the slider button has been retracted from the distal locking position so as to effect initial release of the button slider 42 from the locking position, and, secondly, when the slider button 42 has been fully retracted.

With the button slider 42 in the distal locking position, the pre-mover rack gear 45 is engaged with the teeth of the toothed gear 22 of the mover 20. The inclination of the track along which the button slider 42 can travel, in combination with the provision of the distal notches in the slider track, means that, with the pre-mover in the locking position, slider arm 43 is immobilized so that the toothed gear 22 is substantially locked against rotation due to the pre-mover rack gear 45 holding the toothed gear 22 stationary. Accordingly, the pre-mover 40 functions as a locking device to prevent premature unintentional depression of the trigger 30 and consequential retraction of the sheath pull wire through rotation of the mover reel 21.

The pre-mover finger button 41 may readily be used, however, due to its different alignment to slider arm 43, to proximally retract the button slider 42 along the track provided in the housing, thereby causing slider arm 43 to move proximally, with groove 44 tracing along the pre-mover slider pin 47. This causes the rack gear 45 to rotate the toothed gear 22, at the same time rotating the mover shaft 24 and mover reel 21, in the winding direction.

The track along which button slider 42 is configured to run, and the pre-mover rack gear 45, both have a short fixed length. When the finger button 41 has been retracted to the proximal release position, the slide arm 43 has been displaced proximally to a position in which the rack gear 45 is disposed entirely proximally of the toothed gear 22, and is disengaged therefrom, allowing the toothed gear 22 and mover shaft 24 thereafter to rotate freely of the rack gear 45. (In alternative embodiments where the pre-mover is not implemented by a linear slider, other means may be provided by which to disengage the pre-movement mechanism from the toothed gear 22 or equivalent component. For example, were a pivotally-mounted rack gear to be used, the rack gear might be disengaged by being pivoted downwardly out of mesh with the toothed gear 22 teeth, or in other arrangements might be displaced out of mesh by moving the rack and toothed gear along the toothed gear 22 axis relative to each other.)

The pre-mover 40 is provided in order to effect a small pre-determined rotation of the toothed gear 22 in the winding direction, preferably without effecting any notable retraction or peeling at the sheath distal end or tip. The purpose of the pre-mover 40 is not to effect any bulk movement or retraction of the catheter sheath by winding any substantial portion of the sheath pull wire onto the mover reel 21. Instead, the pre-mover 40 is configured to effect a pre-movement adjustment of the pull wire and catheter sheath relative to the catheter, in preparation for retraction of the sheath using the trigger 30. This adjustment of the sheath pull wire by pre-winding the mover reel 21 by a pre-determined small amount has two effects. Firstly, the initial movement can take up any slack in the sheath pull wire which may have resulted from, or is provided to allow, the flexible bending movements which the catheter undertakes when being folded or inserted into a bodily lumen. Accordingly, any slack in the sheath pull wire is taken up to ensure a taut direct connection between the mover reel 21 and the catheter sheath to be retracted. Secondly, the pre-movement adjustment can further function to pre-tension the catheter, by pre-tensioning the pull wire and the catheter sheath at the distal portion of the catheter, thereby producing a corresponding compressive force along the catheter length, so as to reduce any remaining compressive flexibility along the catheter length. This serves to pre-tension the retraction mechanism, with the sheath pull wire being pulled taut between the sheath and the mover reel 21. With the sheath pull wire pre-tensioned, and with the pre-mover in the proximal release position, the leaf spring 23 functions to prevent motion of the mover reel 21 in the unwinding direction (due to tension in the pull wire), and to maintain the sheath and pull wire in the adjusted pre-tensioned state.

Accordingly, by providing the pre-mover 40, a preliminary adjustment of the sheath pull wire can be effected, to prepare the catheter for sheath retraction. This ensures that subsequent actuation of the trigger 30 will result in a direct corresponding motion of the sheath, as the mover reel 21 winds the sheath pull wire to proximally retract the catheter sheath. This direct pre-tensioned condition provides greater tactile feel for a medical practitioner using the catheter sheath retraction device 1, and improves the accuracy by which the stent being released at the distal end of the device can be positioned and released at the treatment site. The pre-mover 40 further functions to operate as a locking device, securing the retraction mechanism of the catheter sheath retraction device 1 against accidental, premature retraction of the sheath pull wire, such as during transport and during insertion of the catheter into a patient.

From the foregoing, it will be appreciated that the pre-movement adjustment is effected to prepare the stent delivery device provided with such a catheter sheath retraction device for bulk sheath withdrawal and stent release. Although in an ideal configuration the pre-movement adjustment would not cause the catheter sheath to be retracted relative to the catheter, in practice some retraction of the sheath may occur, even to the extent that the stent extreme distal end may become exposed at the catheter distal end portion.

This is to be contrasted, however, with the arrangement in two-stage catheter sheath retraction systems. In such systems, the catheter sheath is firstly partially withdrawn, part way along the stent, using an actuator with a high mechanical advantage so as to effect a controlled withdrawal at a slow rate. By this process, the stent distal end is gradually released from the catheter sheath to expand into contact with the wall of the bodily lumen into which the stent is being implanted, allowing the stent distal end to be positioned at the treatment location with high precision. When the stent distal end has been positioned, the catheter sheath is then secondly withdrawn the remaining distance to fully release the stent, using an actuator with a low mechanical advantage to effect sheath withdrawal at a fast rate. This ensures that once the stent distal end is positioned the stent can be quickly fully released, to reduce the chances of inadvertently causing trauma to the patient through relative movement between the stent and the vessel wall after the stent distal end is engaged with the bodily lumen.

With the pre-movement adjustment presently provided, any sheath retraction is preferably insufficient to expose the stent distal end portion from beneath the sheath. Even if the stent extreme distal end portion is partially exposed, the degree of exposure will be insufficient to allow the stent to expand into circumferential engagement with the wall of the bodily lumen into which the stent is to be implanted. In terms of the stent diameter, the stent is preferably exposed during pre-movement adjustment only by an amount permitting radial expansion by up to 10% or less of the delivery diameter of the stent, more preferably by up to only 5% or less. For typical catheter and stent dimensions, the pre-movement adjustment will represent a maximum sheath withdrawal of 5 mm to 10 mm at the distal end.

Although a specific example of a catheter sheath retraction device 1 has been described and illustrated, it will be appreciated that numerous modifications may be effected based upon the same operational principles by which the described device functions.

For example, the pre-mover 40 may be provided by alternative means for adjusting the sheath pull wire prior to bulk retraction of the sheath relative to the catheter, other than by using a slider arm 43 and rack gear 45. Even if a rack gear based mechanism is utilized, the slider arm need not be configured to provide a secure locking function, and alternative locking devices may be utilized. Similarly, the pre-mover button could be mounted at the proximal end of the catheter sheath retraction device, to adjust the mover 20 by a proximal pulling retraction, rather than a proximal pushing retraction of the rack gear 45. Numerous further alternatives are clearly possible.

Similarly, the advantages achieved by the pre-mover 40 are not restricted to embodiments utilizing a trigger 30 for actuating the mover reel 20 to retract the sheath pull wire. Various actuation mechanisms utilizing thumb wheels, knobs, triggers and sliders are known for retracting a sheath pull wire, of which the skilled reader will be fully aware.

A number of published documents have been mentioned above. Many of these are from the present proprietor, and represent steps along the way to the present invention. It is intended that the disclosures of these mentioned earlier documents are incorporated by reference in their entirety into the teaching and disclosure of the present specification, as if each individual publication or patent application were specifically and individually put forth herein.

What is claimed is:

1. A device comprising:
   a reel that rotates and winds up a wound length of an elongate member; and
   a limiter that limits reel rotation after the reel winds up the wound length, wherein:
      the limiter comprises a tether connected to the reel through a line connector,
      the reel winds up the tether until, when taut, the tether prevents further rotation,
      the tether has a total length greater than a consumable length and the consumable length corresponds to the wound length, and the tether has reference markings indicating different consumable lengths corresponding to different wound lengths, the consumable lengths set by consuming the tether up to the reference markings indicating an amount of remaining consumable length, which corresponds to the wound length.

2. The device of claim 1, wherein the tether is wound on a spool and reel rotation winds the tether from the spool onto the reel.

3. The device of claim 2, wherein the device further comprises a sheath disposed around a stent, and wherein the elongate member is a sheath retraction wire connected to the sheath.

4. A surgical apparatus including the device of claim 3, comprising a housing and a mover connected to a catheter.

5. The surgical apparatus of claim 4, wherein the stent is releasably disposed on the catheter, and wherein the stent is released by moving the sheath retraction wire respective to the catheter.

6. The surgical apparatus of claim 5, wherein:
the stent is a self-expanding stent,
the device is configured for a pre-movement adjustment of the sheath retraction wire relative to the catheter, and
the pre-movement adjustment is insufficient to release any part of the stent to an expanded diameter exceeding 110% of an unexpanded stent diameter.

7. The surgical apparatus of claim 6, wherein the pre-movement adjustment is insufficient to release any part of the stent.

8. The device of claim 1, further comprising a sheath disposed around a stent, wherein:
the elongate member is a sheath retraction wire connected to the sheath that retracts the sheath as the reel winds up the sheath retraction wire, and
the device limits retraction of the sheath using the limiter that limits a wound length of the sheath retraction wire to the consumable length.

* * * * *